(12) United States Patent
Chen

(10) Patent No.: US 11,279,763 B2
(45) Date of Patent: Mar. 22, 2022

(54) INTEGRIN ALPHA 9 BLOCKADE SUPPRESSES LYMPHATIC VALVE FORMATION AND PROMOTES TRANSPLANT SURVIVAL

(71) Applicant: The Regents of the University of California, Oakland, CA (US)

(72) Inventor: Lu Chen, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/344,741

(22) PCT Filed: Oct. 26, 2017

(86) PCT No.: PCT/US2017/058553
§ 371 (c)(1),
(2) Date: Apr. 24, 2019

(87) PCT Pub. No.: WO2018/081436
PCT Pub. Date: May 3, 2018

(65) Prior Publication Data
US 2019/0270819 A1 Sep. 5, 2019

Related U.S. Application Data

(60) Provisional application No. 62/413,863, filed on Oct. 27, 2016.

(51) Int. Cl.
| | |
|---|---|
| *C07K 16/28* | (2006.01) |
| *A61P 27/02* | (2006.01) |
| *A61K 9/00* | (2006.01) |
| *A61K 45/06* | (2006.01) |
| *C12N 15/113* | (2010.01) |
| *A61K 39/00* | (2006.01) |

(52) U.S. Cl.
CPC ........ *C07K 16/2839* (2013.01); *A61K 9/0019* (2013.01); *A61K 9/0048* (2013.01); *A61K 45/06* (2013.01); *A61P 27/02* (2018.01); *C12N 15/113* (2013.01); *A61K 2039/505* (2013.01); *C07K 2317/54* (2013.01); *C07K 2317/56* (2013.01); *C07K 2317/73* (2013.01); *C07K 2317/76* (2013.01); *C12N 2310/14* (2013.01)

(58) Field of Classification Search
CPC .......... A61K 2039/505; A61K 2300/00; A61P 27/02; C12N 5/069; C12N 15/113; C12N 2310/14; C07K 2317/76
USPC ........... 350/387.5; 435/6.1, 91.1, 91.31, 455, 435/458; 514/44 A; 536/23.1, 24.5
See application file for complete search history.

(56) References Cited

U.S. PATENT DOCUMENTS

| | | | |
|---|---|---|---|
| 2005/0004027 A1* | 1/2005 | Wiegand | ................. A61P 41/00 514/8.1 |
| 2015/0225377 A1 | 8/2015 | Foitzik et al. | |

OTHER PUBLICATIONS

Bazigou, E , et al., "Integrin-alpha 9 is Required for Fibronectin Matrix Assembly during Lymphatic Valve Morphogenesis", Developmental Cell 17, 175-186 (2009).

(Continued)

*Primary Examiner* — Jane J Zara
(74) *Attorney, Agent, or Firm* — Viksnins Harris Padys Malen LLP

(57) ABSTRACT

In certain embodiments, the present invention provides methods of suppressing valvulogenesis (VG) in a lymphatic vessel in an inflamed or transplanted tissue or organ in a mammal in need thereof comprising administering an effective amount of an anti-integrin alpha 9 (Itga-9) therapeutic agent to the mammal, and optionally by administering anti-VEGFR-3 agent.

14 Claims, 12 Drawing Sheets
Specification includes a Sequence Listing.

(56) References Cited

OTHER PUBLICATIONS

Chen, L, et al., "Vascular endothelial growth factor receptor-3 mediates induction of corneal alloimmunity", Nature Medicine 10(8), 813-815 (2004).

Makinen, T, et al., "Inhibition of lymphangiogenesis with resulting lymphedema in transgenic mice expressing soluble VEGF receptor-3", Nature Medicine 7(2), 199-205 (2001).

Ou, J, et al., "Endostatin Suppresses Colorectal Tumor-Induced Lymphangiogenesis by Inhibiting Expression of Fibronectin Extra Domain A and Integrin alpha 9", J Cell Biochem 112, 2106-2114 (2011).

Ou, J, et al., "Neuropilin-2 mediates lymphangiogenesis of colorectal carcinoma via a VEGFC/VEGFR3 independent signaling", Cancer Letters 358, 200-209 (2015).

Truong, T, et al., "Novel Characterization of Lumphatic Valve Formation during corneal Inflammation", PLOS One 6 (7), e21918 (2011).

Altiok, et al., "Integrin Alpha-9 Mediates Lymphatic Valve Formation in Corneal Lymphangiogenesis", Invest Ophthalmol Vis Sci 56(11), 6313-6319 (2015).

Kang, G, et al., "Integrin Alpha 9 Blockade Suppresses Lymphatic Valve Formation and Promotes Transplant Survival", Invest Opthalmol Vis Sci 57(14), 5935-5939 (2016).

Kang, G, et al., "Live Imaging of Lymphatic Valve Formation after Corneal Transplantation", Investigative Ophthalmology & Visual Science 54(15), 2096 (2013).

Patent Cooperation Treaty, International Searching Authority, Search Report and Written Opinion for PCT/US2017/58553, 11 pages, dated March 5, 2018.

Yan, A, et al., "Mechanisms of Lymphatic Regeneration after Tissue Transfer", PLoS One 6(2), e17201, 12 pages (2011).

Zhang, H, et al., "Combined Blockade of VEGFR-3 and VLA-1 Markedly Promotes High-Risk Corneal Transplant Survival.", Invest Ophthalmol Vis Sci 52(9), 6529-6535 (2011).

Wu, J, et al., "Effect of integrin $\alpha 9\beta 1$ on the lymphangiogenesis and expression of vascular endothelial growth factor C after corneal suture", Medical Journal of Chinese People's Liberation Army. vol. 37, No. 5 (2012). [English Abstract].

* cited by examiner

A

B

C

A

B

A

B

A

B

A

B ns ally sponsored research and subject to certain rights...

SEQUENCE LISTING

```
<160> NUMBER OF SEQ ID NOS: 5

<210> SEQ ID NO 1
<211> LENGTH: 21
<212> TYPE: DNA
<213> ORGANISM: Homo sapiens

<400> SEQUENCE: 1
aagaagaaag tcgtactata g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggaatcatg tctccaacct                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctctgcacc accagatgag                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatctggcac cacaccttct                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggggtgttga aggtctcaaa                                                20
```

INTEGRIN ALPHA 9 BLOCKADE SUPPRESSES LYMPHATIC VALVE FORMATION AND PROMOTES TRANSPLANT SURVIVAL

CROSS-REFERENCE TO RELATED APPLICATION

This application claims priority to U.S. Provisional Application No. 62/413,863 that was filed on Oct. 27, 2016. The entire content of the application referenced above is hereby incorporated by reference herein.

STATEMENT REGARDING FEDERALLY SPONSORED RESEARCH

This invention was made with government support under EY017392 awarded by National Institutes of Health and W81XWH-14-1-0496 awarded by Department of Defense. The government has certain rights in the invention.

The instant application contains a Sequence Listing which has been submitted electronically in ASCII format and is hereby incorporated by reference in its entirety. Said ASCII copy, created on Dec. 13, 2017, is named 17733_003WO1_SL.txt and is 1,406 bytes in size.

BACKGROUND OF THE INVENTION

The lymphatic network penetrates most tissues and its dysfunction is associated with a broad spectrum of disorders, such as cancer metastasis, inflammation, transplant rejection, hypertension, obesity, and lymphedema. After being neglected for centuries due to historical reasons and technical limitations, lymphatic research has gained significant attention and great progress in recent years. However, currently, few treatments exist for lymphatic diseases. Accordingly, new treatments for lymphatic diseases and to prevent transplantation rejection are needed.

SUMMARY OF THE INVENTION

The present invention provides in certain embodiments a method of suppressing valvulogenesis (VG) in a lymphatic vessel in a transplanted tissue or organ in a mammal in need thereof comprising administering an effective amount of an anti-integrin alpha 9 (Itga-9) therapeutic agent to the mammal.

The present invention provides in certain embodiments a method of inhibiting integrin alpha 9 (Itga-9) in a lymphatic vessel comprising contacting the lymphatic vessel with anti-Itga-9 therapeutic agent.

The present invention provides in certain embodiments a method of preventing or treating corneal valvulogenesis (VG) in a mammal in need thereof comprising administering an effective amount of a therapeutic agent comprising an anti-Itga-9 antibody to the mammal.

The present invention provides in certain embodiments a composition comprising a therapeutic agent comprising an anti-Itga-9 binding agent for use in the therapeutic treatment of pathological lymphatic formation in a tissue or organ.

The present invention provides in certain embodiments a use of an anti-Itga-9 binding agent to prepare a medicament useful for inhibiting LG in a mammal.

The present invention provides in certain embodiments a composition comprising a therapeutic agent and an anti-Itga-9 binding agent for use in medical therapy.

The present invention provides in certain embodiments a method of inhibiting transplant rejection in a mammal in need thereof comprising administering an effective amount of a therapeutic agent to the mammal, wherein the therapeutic agent is an anti-Itga-9 therapeutic agent.

"Treating" as used herein refers to ameliorating at least one symptom of, curing and/or preventing the development of VG.

In certain embodiments, the method further comprising administering VEGFR-3.

BRIEF DESCRIPTION OF DRAWINGS

(FIG. 1A) Representative whole-mount immunostaining images demonstrating significantly fewer valves in the Itga-9 blocking antibody treated cornea in comparison to isotype control treated cornea. Red: Itga-9; Green: LYVE-1. Scale bars, 100 µm. (FIG. 1B) Comparative quantification on lymphatic valves and lymphatic vessel invasion area in control and treatment condition. Anti-Itga-9 treatment only reduced valve formation. The experiment was repeated twice with 7 mice in control and 8 mice in treatment group. *P<0.05; n.s.: not significant. (FIG. 1C) Comparative quantification showing significant lower ratio of valves to lymphatic invasion area in response to anti-Itga-9 treatment. The experiment was repeated twice with 7 mice in control and 8 mice in treatment group. *P<0.05.

(FIG. 2A) Schematic illustration of nasal and temporal quadrant areas used for quantification. Eight short lines around the clock indicate sutures placed along the graft border. Outer solid circle: limbus. Inner dotted circle: graft border. Vertical line: separation between the nasal and temporal sides. Grey shaded regions: nasal and temporal areas evaluated. (FIG. 2B) Comparative quantification showing significantly greater lymphatic invasion area in the nasal than the temporal side in both control and treatment condition. The experiment was repeated twice with 7 mice in control and 8 mice in treatment group. *P<0.05.

(FIG. 3A) Representative images from slitlamp examination of rejected and survived grafts in control and treatment condition, respectively. (FIG. 3B) Kaplan-Meier survival curves showing significantly higher survival rate in the treatment group. *P<0.05.

(FIG. 7A) Representative immunofluorescent microscopic images showing significantly fewer valves in the Itga-9 blocking antibody treated cornea, as compared with control isotype treated sample. Red: Itga-9; Green: LYVE-1. Scale bars, 50 lm. (FIG. 7B) Summarized data quantifying valve formation. *P<0.05.

(FIG. 8A) Representative immunocytofluorescent microscopic images showing Itga-9 expression in human LECs. Red: Itga-9; Blue: DAPI. Scale bars, 50 lm. (FIG. 8B) Real-time PCR analysis showing Itga-9 gene knockdown with Itga-9 siRNA, compared with scrambled siRNA. *P<0.05.

(FIG. 9A) Flow cytometric analysis with the Guava ViaCount assay showing no significant difference in cell viability between the control and Itga-9 siRNA transfected cells at 48 hours posttransfection. Summarized data from repetitive experiments are presented in FIG. 9B. n.s., not significant.

(FIG. 10A) Summarized data showing significant suppression of LEC proliferation following transfection with Itga-9 siRNA using MTS proliferation assay. *P<0.05. (FIG. 10B) Summarized data showing significant reduction of LEC adhesion to fibronectin after transfection with Itga-9 siRNA. *P<0.05.

(FIG. 11A) Summarized data showing significant reduction in LEC migration over a 72-hour period using scratch assay. *P<0.05. (FIG. 11B) Representative images of cell migration at 72 hours. Scale bars, 100 lm. Red: TRITC-conjugated phalloidin.

(FIG. 12A) Representative microscopic images showing significant reduction of tube formation on Matrigel. Scale bars, 500 lm. (FIG. 12B) Summarized data on total tube length. *P<0.05.

DETAILED DESCRIPTION

Figure 1A:
FIGS. 1A-1C. Lymphatic valvulogenesis was suppressed by Itga-9 blockade after corneal transplantation.

Unlike blood vessels which have been studied for centuries in the past, lymphatic research denotes a field of new discovery and has experienced exponential growth in recent years (Alitalo, K. The lymphatic vasculature in disease. Nat. Med. 2011; 17:1371-1380; Tammela T, Alitalo K: Lymphangiogenesis: Molecular mechanisms and future promise. Cell 2010; 140:460-476; Chen L: Ocular Lymphatics: State-of-the-Art Review. Lymphology 2009; 42:66-76; Alitalo K, Tammela T, Petrova T V: Lymphangiogenesis in development and human disease; Nature 2005; 438:946-953; Brown P: Lymphatic system: unlocking the drains. Nature 2005; 436:456-458; Folkman J, Kaipainen A: Genes tell lymphatics to sprout or not. Nat Immunol 2004; 5:11-12; Rockson S G: The broad spectrum of lymphatic health and disease. Lymphat Res Biol; 8:101). The lymphatic network penetrates most tissues in the body and plays critical roles in a broad spectrum of functions, such as immune surveillance, body fluid regulation, and fat and vitamin absorption. Numerous diseases and conditions are therefore associated with lymphatic dysfunction, which include but are not limited to cancer metastasis, tissue and major organ (heart, kidney and lung) transplant rejection, inflammatory and immune diseases, infections, asthma, obesity, diabetes, AIDS, hypertension and lymphedema. These disorders can be disabling, disfiguring, and even life threatening. To date, there is little effective treatment for lymphatic disorders, so it is a field with an urgent demand for new therapeutic protocols.

The cornea provides an ideal site for lymphatic research due to its accessible location, transparent nature, and lymphatic-free but inducible features (Chen L: Ocular Lymphatics: State-of-the-Art Review. Lymphology 2009; 42:66-76; Rogers M S, Birsner A E, D'Amato R J: The mouse cornea micropocket angiogenesis assay. Nat Protoc 2007; 2:2545-2550; Cursiefen C, Chen L, Dana M R, Streilein J W: Corneal lymphangiogenesis: evidence, mechanisms, and implications for corneal transplant immunology. Cornea 2003; 22:273-281; Chen L, Hann B, Wu L: Experimental models to study lymphatic and blood vascular metastasis, in "From local invasion to metastatic cancer". Stanley P. L. Leong (Editor), Humana Press. 2011). The success of using the cornea for lymphatic research can be predicted from the fact that during past centuries, more than one third of basic knowledge on blood vessels was obtained from studies with the cornea, as estimated by Judah Folkman, the grandfather of tumor angiogenesis research.

Though not supplied by lymphatic vessels under normal condition, lymphatic formation (lymphangiogenesis, LG) accompanies many corneal diseases after an inflammatory, infectious, traumatic, immunogenic, or chemical damage. Once induced, they enhance high volume delivery of immune cells and mediate transplant rejection as well. Collective data have shown that the lymphatic pathway is a primary mediator of corneal transplant rejection (Dietrich T, Bock F, Yuen D, et al.: Cutting edge: lymphatic vessels, not blood vessels, primarily mediate immune rejections after transplantation. J Immunol 2010; 184:535-539; Zhang H, Grimaldo S, Yuen D, Chen L: Combined blockade of VEGFR-3 and VLA-1 markedly promotes high-risk corneal transplant survival. Invest Ophthalmol Vis Sci 2011). Moreover, LG has been associated with transplant rejection in other parts of the body (such as kidney, heart, lung, bone implant) (Kerjaschki D: Lymphatic neoangiogenesis in renal transplants: a driving force of chronic rejection? J Nephrol 2006; 19:403-406; Kerjaschki D, Huttary N, Raab I, et al.: Lymphatic endothelial progenitor cells contribute to de novo lymphangiogenesis in human renal transplants. Nat Med 2006; 12:230-234; Jell G, Kerjaschki D, Revell P, Al-Saffar N: Lymphangiogenesis in the bone-implant interface of orthopedic implants: importance and consequence. J Biomed Mater Res A 2006; 77:119-127; Geissler H J, Dashkevich A, Fischer U M, et al.: First year changes of myocardial lymphatic endothelial markers in heart transplant recipients. Eur J Cardiothorac Surg 2006; 29:767-771).

Corneal transplantation is the most common form among all solid organ and tissue transplantation. Although it enjoys a high survival rate in uninflamed and alymphatic host reds, the rejection rate can be as high as 50-90% when the grafting is performed on inflamed and lymphatic-rich corneas. To date, there is still few effective management of this high rejection situation. Unfortunately, many patients who are blind as a result of corneal diseases fall in this high-rejection category (after a traumatic, inflammatory, infectious, or chemical damage). Due to the poor prognosis, these patients are not even considered as good candidates for the transplantation surgery and have to give up their hope for vision restoration. We are therefore interested in identifying new therapeutic targets to treat LG and its related disorders including graft rejection. The cornea offers an ideal site for LG research. Due to its accessible location, transparent nature, and alymphatic feature under normal condition, this tissue provides a favorable model to study inducible lymphatic growth without having to distinguish from pre-existing or background vessels (Chen L. Ocular lymphatics: state-of-the-art review. Lymphology 2009; 42:66-76). Corneal LG can be induced by a number of pathological insults, such as inflammation, infection, trauma, and chemical burns, and it is a primary mediator of transplant rejection (Chen L. Ocular lymphatics: state-of-the-art review. Lymphology 2009; 42:66-76; Dietrich T, Bock F, Yuen D, et al. Cutting edge: lymphatic vessels, not blood vessels, primarily mediate immune rejections after transplantation. J Immunol 2010; 184:535-539; Yuen D, Pytowski B, Chen L. Combined blockade of VEGFR-2 and VEGFR-3 inhibits inflammatory lymphangiogenesis in early and middle stages. Invest Ophthalmol Vis Sci 2011; 52:2593-2597).

This invention has a number of potential applications, such as preventing or treating corneal valvulogenesis (VG) to promote transplant survival.

The present invention provides in certain embodiments a method of suppressing valvulogenesis (VG) in a lymphatic vessel in a transplanted tissue or organ in a mammal in need thereof comprising administering an effective amount of an anti-integrin alpha 9 (Itga-9) therapeutic agent to the mammal.

In certain embodiments, the lymphatic vessel is in eye tissue.

In certain embodiments, the eye tissue is corneal tissue.

In certain embodiments, the transplanted tissue is a cornea transplant.

In certain embodiments, the anti-Itga-9 therapeutic agent is a binding agent specific for Itga-9.

In certain embodiments, the binding agent is an antibody or antibody fragment.

In certain embodiments, the binding agent is an RNAi molecule that inhibits the production or activity of Itga-9.

In certain embodiments, the therapeutic agent is administered by subconjunctival injection.

In certain embodiments, VG is suppressed by at least 10%, as compared to a control vessel.

In certain embodiments, the number of lymphatic valves is reduced by at least 10% as compared to an untreated control.

In certain embodiments, the number of lymphatic vessels is comparable to an untreated control.

The present invention provides in certain embodiments a method of inhibiting integrin alpha 9 (Itga-9) in a lymphatic vessel comprising contacting the lymphatic vessel with anti-Itga-9 therapeutic agent.

The present invention provides in certain embodiments a method of preventing or treating corneal valvulogenesis (VG) in a mammal in need thereof comprising administering an effective amount of a therapeutic agent comprising an anti-Itga-9 antibody to the mammal.

In certain embodiments, the corneal VG is induced by transplantation, inflammation, infection, dry eye, trauma, or chemical damage.

In certain embodiments, the mammal is a human.

In certain embodiments, the therapeutic agent is present within a pharmaceutical composition.

In certain embodiments, the administration is by local or systemic administration.

In certain embodiments, administration is by subconjunctival, intraocular, periocular, retrobulbar, intramuscular, topical, intravenous, intraperitoneal or subcutaneous administration.

In certain embodiments, the method further comprises administering of another synergistic factor, e.g. VEGFR-3.

The present invention provides in certain embodiments a composition comprising a therapeutic agent comprising an anti-Itga-9 binding agent for use in the therapeutic treatment of pathological lymphatic formation in a tissue or organ.

In certain embodiments, the composition further comprises another synergistic factor, e.g. VEGFR-3.

The present invention provides in certain embodiments a use of an anti-Itga-9 binding agent to prepare a medicament useful for inhibiting LG in a mammal.

The present invention provides in certain embodiments a use of an anti-Itga-9 binding agent and another synergistic factor, e.g. VEGFR-3 to prepare a medicament useful for inhibiting LG in a mammal. The present invention provides in certain embodiments a composition comprising a therapeutic agent an anti-Itga-9 binding agent for use in medical therapy.

In certain embodiments, the composition further comprises another synergistic factor, e.g. VEGFR-3.

The present invention provides in certain embodiments a method of inhibiting transplant rejection in a mammal in need thereof comprising administering an effective amount of a therapeutic agent to the mammal, wherein the therapeutic agent is an anti-Itga-9 therapeutic agent.

In certain embodiments, the method further comprises administering of another synergistic factor, e.g. VEGFR-3.

The present inventors have discovered that integrin alpha 9 blockade suppresses lymphatic valve formation and promotes transplant survival. The present data indicate that Itga-9 blocking agents can be used to suppress pathological lymphatic valve formation in the tissue such as the cornea. Itga-9 blocking agents can be administered locally or systemically to treat eye diseases (subconjunctival, intraocular, periocular, retrobulbar, intramuscular, topical, intravenous, subcutaneous, etc.). The invention can also be used to treat other lymphatic disorders in the body, such as cancer metastasis, and inflammatory and immune diseases. Itga-9 blocking strategy may be potentially used to inhibit lymphatic valve formation and treat lymphatic disorders, such as transplant rejection. In certain embodiments, valvulogenesis (VG) is suppressed by at least 10%. In certain embodiments, VG is suppressed by at least 10%, 15%, 20%, 25%, 30%, 35%, 40%, 45%, 50%, 55%, 60%, 65%, 70%, 75%, 80%, 85%, 90% 95%, 99% or 100% In certain embodiments, VG is suppressed at a level sufficient to cause a therapeutic effect. As used herein the term "therapeutic effect" refers to a change in the associated abnormalities of the disease state, including pathological and behavioral deficits; a change in the time to progression of the disease state; a reduction, lessening, or alteration of a symptom of the disease; or an improvement in the quality of life of the person afflicted with the condition. Therapeutic effects can be measured quantitatively by a physician or qualitatively by a patient afflicted with VG targeted by the blocking agent.

In one embodiment, the invention features a method for treating or preventing VG in a subject or organism comprising, contacting the subject or organism with an Itga-9 blocking agent molecule of the invention via local administration to relevant tissues or cells, for example, by administration of an Itga-9 blocking agent to relevant cells.

Methods of delivery of Itga-9 blocking agents include, but are not limited to, intravenous administration and administration directly into a patient's eye.

Binding Agents

The present invention provides a purified binding agent (or ligand) that binds specifically to Itga-9, i.e., an "anti-Itga-9 therapeutic agent." The anti-Itga-9 therapeutic agent can be an antibody or a small molecule agent. Examples of agents that are anti-Itga-9 therapeutic agents include monoclonal or polyclonal antibodies, peptides, small molecules, small interfering RNAs, etc.

Antibodies

As used herein, the term "antibody" includes scFv, humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv or "nanobody"), humanized, fully human or chimeric antibodies, single-chain antibodies, diabodies, and antigen-binding fragments of antibodies (e.g., Fab fragments). A scFv is a fusion protein of the variable region of the heavy ($V_H$) and light chains ($V_L$) of an immunoglobulin that is connected by means of a linker peptide. The linker is usually short, about 10-25 amino acids in length. If flexibility is important, the linker will contain a significant number of glycines. If solubility is important, serines or theonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). Holliger et al., "Diabodies: small bivalent and bispecific antibody fragments," PNAS, July 1993, 90:6444-6448. Bivalency allows antibodies to bind to multimeric antigens with high avidity, and bispecificity allows the cross-linking of two antigens.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

Polyclonal and monoclonal antibodies can be prepared by methods known to those skilled in the art.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

The antibodies of the present invention also include antibodies which comprise complementarity-determining regions (CDRs), or regions functionally equivalent to CDRs. The term "functionally equivalent" refers to comprising amino acid sequences similar to the amino acid sequences of CDRs of any of the monoclonal antibodies isolated in the Examples. The term "CDR" refers to a region in an antibody variable region (also called "V region"), and determines the specificity of antigen binding. The H chain and L chain each have three CDRs, designated from the N terminus as CDR1, CDR2, and CDR3. There are four regions flanking these CDRs: these regions are referred to as "framework," and their amino acid sequences are highly conserved. The CDRs can be transplanted into other antibodies, and thus a recombinant antibody can be prepared by combining CDRs with the framework of a desired antibody. One or more amino acids of a CDR can be modified without losing the ability to bind to its antigen. For example, one or more amino acids in a CDR can be substituted, deleted, and/or added.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity (Mark D. F. et al., Proc. Natl. Acad. Sci. U.S.A. 81:5662-5666 (1984); Zoller M. J. and Smith M., Nucleic Acids Res. 10: 6487-6500 (1982); Wang A. et al., Science 224: 1431-1433; Dalbadie-McFarland G. et al., Proc. Natl. Acad. Sci. U.S.A. 79: 6409-6413 (1982)). The number of mutated amino acids is not limited, but in general, the number falls within 40% of amino acids of each CDR, and preferably within 35%, and still more preferably within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., Nature 321: 522-525 (1986); Reichmann et al., Nature 332: 323-329 (1988); Presta Curr. Op. Struct. Biol. 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., Cancer Res. (1993) 53, 851-856).

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., Journal of Biochemical and Biophysical Methods 24:107-117 (1992); Brennan et al., Science 229:81 (1985); Co, M. S. et al., J. Immunol., 1994, 152, 2968-2976; Better, M. & Horwitz, A. H., Methods in Enzymology, 1989, 178, 476-496, Academic Press, Inc.; Plueckthun, A. & Skerra, A., Methods in Enzymology, 1989, 178, 476-496, Academic Press, Inc.; Lamoyi, E., Methods in Enzymology, 1989, 121, 663-669; Bird, R. E. et al., TIBTECH, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')2. Other chemically crosslinked antibody fragments are also known to those skilled in the art. Pepsin digestion of an antibody yields two fragments; one is a F(ab')2 fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab')$_2$-SH fragments can be recovered directly from hosts, such as *E. coli*, and then allowed to form F(ab')$_2$ fragments by chemical crosslinking (Carter et al., Bio/Technology 10:163-167 (1992)). In an alternative method, F(ab')2 fragments can be isolated directly from a culture of recombinant hosts.

The term "diabody (Db)" refers to a bivalent antibody fragment constructed by gene fusion (for example, P. Holliger et al., Proc. Natl. Acad. Sci. USA 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., Proc. Natl. Acad. Sci. U.S.A, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

RNA Interference (RNAi) Molecules

An RNAi molecule may be a "small interfering RNA" or "short interfering RNA" or "siRNA" or "short hairpin RNA" or "shRNA" or "microRNA" or "miRNA." An RNAi molecule an RNA duplex of nucleotides that is targeted to a nucleic acid sequence of interest, for example, Itga-9. As used herein, the term "RNAi molecule" is a generic term that encompasses the subset of shRNAs. A "RNA duplex" refers to the structure formed by the complementary pairing between two regions of a RNA molecule. RNAi molecule is "targeted" to a gene in that the nucleotide sequence of the duplex portion of the RNAi molecule is complementary to a nucleotide sequence of the targeted gene. In certain embodiments, the RNAi molecules are targeted to the sequence encoding Itga-9. In some embodiments, the length of the duplex of RNAi molecules is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the RNAi molecule can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

The RNAi molecule can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where RNAi molecules have not been administered). Knock-down of gene expression can be directed, for example, by the use of dsRNAs, siRNAs or miRNAs.

"RNA interference (RNAi)" is the process of sequence-specific, post-transcriptional gene silencing initiated by an RNAi molecule. During RNAi, RNAi molecules induce degradation of target mRNA with consequent sequence-specific inhibition of gene expression. RNAi involving the use of RNAi molecules has been successfully applied to knockdown the expression of specific genes in plants, *D. melanogaster*, *C. elegans*, trypanosomes, planaria, hydra, and several vertebrate species including the mouse.

According to a method of the present invention, the expression of Itga-9 can be modified via RNAi. For example, the accumulation of Itga-9 can be suppressed in a cell. The term "suppressing" refers to the diminution, reduction or elimination in the number or amount of transcripts present in a particular cell. For example, the accumulation of mRNA encoding Itga-9 can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "chimeric" refers to a gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

A "foreign" gene refers to a gene not normally found in the host organism that has been introduced by gene transfer.

The terms "protein," "peptide" and "polypeptide" are used interchangeably herein.

"Conservatively modified variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNAi molecule. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "open reading frame" (ORF) refers to the sequence between translation initiation and termination codons of a coding sequence. The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m 81.5°\ C.+16.6(\log M)+0.41(\%\ GC)-0.61(\%\ form)-500/L;$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., *E. coli*) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference. In some embodiments, gene silencing may be allele-specific. "Allele-specific" gene silencing refers to the specific silencing of one allele of a gene.

"Knock-down," "knock-down technology" refers to a technique of gene silencing in which the expression of a target gene is reduced as compared to the gene expression prior to the introduction of the RNAi molecule, which can lead to the inhibition of production of the target gene product. The term "reduced" is used herein to indicate that the target gene expression is lowered by 1-100%. For example, the expression may be reduced by 10, 20, 30, 40, 50, 60, 70, 80, 90, 95, or even 99%. Knock-down of gene expression can be directed by the use of dsRNAs or siRNAs. For example, "RNA interference (RNAi)," which can involve the use of siRNA, has been successfully applied to knockdown the expression of specific genes in plants, *D. melanogaster, C. elegans*, trypanosomes, planaria, hydra, and several vertebrate species including the mouse.

"RNA interference (RNAi)" is the process of sequence-specific, post-transcriptional gene silencing initiated by siRNA. RNAi is seen in a number of organisms such as *Drosophila*, nematodes, fungi and plants, and is believed to be involved in anti-viral defense, modulation of transposon activity, and regulation of gene expression. During RNAi, RNAi molecules induce degradation of target mRNA with consequent sequence-specific inhibition of gene expression.

A "small interfering" or "short interfering RNA" or siRNA is a RNA duplex of nucleotides that is targeted to a gene interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. The "sense" and "antisense" sequences can be used with or without a loop region to form siRNA molecules. As used herein, the term siRNA is meant to be equivalent to other terms used to describe nucleic acid molecules that are capable of mediating sequence specific RNAi, for example, double-stranded RNA (dsRNA), micro-RNA (miRNA), short hairpin RNA (shRNA), short interfering oligonucleotide, short interfering nucleic acid, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetic silencing. For example, siRNA molecules of the invention can be used to epigenetically silence genes at both the post-transcriptional level or the pre-transcriptional level. In a non-limiting example, epigenetic modulation of gene expression by siRNA molecules of the invention can result from siRNA mediated modification of chromatin structure or methylation pattern to alter gene expression. In another non-limiting example, modulation of gene expression by siRNA molecules of the invention can result from siRNA mediated cleavage of RNA (either coding or non-coding RNA) via RISC, or alternately, translational inhibition as is known in the art.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Treating" as used herein refers to ameliorating at least one symptom of, curing and/or preventing the development of a disease or a condition.

The RNAi molecules of the present invention can be generated by any method known to the art, for example, by in vitro transcription, recombinantly, or by synthetic means. In one example, the RNAi molecules can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13mp18 and M13mp19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101.

There are well-established criteria for designing siRNAs. However, since the mechanism for siRNAs suppressing gene expression is not entirely understood and siRNAs selected from different regions of the same gene do not work as equally effective, very often a number of siRNAs have to be generated at the same time in order to compare their effectiveness.

Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, and prophylactic processes (i.e., prevention of a disease or of an undesired medical condition). A gene "associated with a condition" is a gene that is either the cause, or is part of the cause, of the condition to be treated. Examples of such genes include genes associated with Itga-9. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Formulations and Methods of Administration

The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved.

The present invention envisions treating LG in a mammal by the administration of an agent, e.g., an antibody or antibody fragment. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

For in vivo use, a therapeutic agent as described herein is generally incorporated into a pharmaceutical composition prior to administration. Within such compositions, one or more therapeutic compounds as described herein are present as active ingredient(s) (i.e., are present at levels sufficient to provide a statistically significant effect on the symptoms of cystic fibrosis, as measured using a representative assay). A pharmaceutical composition comprises one or more such compounds in combination with any pharmaceutically acceptable carrier(s) known to those skilled in the art to be suitable for the particular mode of administration. In addition, other pharmaceutically active ingredients (including other therapeutic agents) may, but need not, be present within the composition.

The term "therapeutically effective amount," in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The terms "treat," "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

In certain embodiments, the present therapeutic agent may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered by injection or infusion (e.g. intravenously, subcutaneously, or intraperitoneally). Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

Example 1

Abstract

Purpose.

The lymphatic pathway mediates transplant rejection. We recently reported that lymphatic vessels develop luminal valves in the cornea during lymphangiogenesis, and these valves express integrin alpha 9 (Itga-9) and play a critical role in directing lymph flow. In this study, we used an allogeneic corneal transplantation model to investigate whether Itga-9 blockade could suppress valvulogenesis after transplantation, and how this effect would influence the outcomes of the transplants.

Methods.

Orthotopic corneal transplantation was performed between fully mismatched C57BL/6 (donor) and BALB/c (recipient) mice. The recipients were randomized to receive subconjunctival injections of either Itga-9 blocking antibody or isotype control twice a week for 8 weeks. Corneal grafts were assessed in vivo by ophthalmic slit-lamp biomicroscopy and analyzed using Kaplan-Meier survival curves. Additionally, whole-mount full thickness corneas were evaluated ex vivo by immunofluorescent microscopy on both lymphatic vessels and valves.

Results.

Anti-Itga-9 treatment suppressed lymphatic valvulogenesis after transplantation. Our treatment did not affect lymphatic vessel formation or their nasal polarized distribution in the cornea. More importantly, Itga-9 blockade led to a significant promotion of graft survival.

Conclusions.

Lymphatic valvulogenesis is critically involved in transplant rejection. Itga-9 targeting may offer a new and effective strategy to interfere with the immune responses and promote graft survival.

Introduction

The lymphatic vasculature system has essential functions in maintaining body fluid homeostasis, dietary fat absorption, and immune surveillance. Dysfunction of lymphatic system has been found in a wide array of diseases and disorders from cancer metastasis to inflammation and transplant rejection. In transplantation, graft failure is mainly due to rejection, but the existing treatments are of limited efficacy. Studies have shown that transplantation immunity can be modulated by a molecular blockade of the lymphatic pathway, and lymphatic vessels has emerged as one of a key modulators for the development of new therapeutic strategies.

While most of the studies have been focused on the regulation of the formation of the lymphatic vessels, or lymphangiogenesis (LG), we have recently revealed that lymphatic vessels develop luminal valves as LG progresses, and these valves play a crucial role in guiding the flow of the lymph inside the vessels, which contains immune cells and antigens for immune responses. (Truong T, Altiok E, Yuen D, Ecoiffier T, Chen L. Novel characterization of lymphatic valve formation during corneal inflammation. PloS one 2011; 6:e21918; Kang G J, Ecoiffier T, Truong T, et al. Intravital Imaging Reveals Dynamics of Lymphangiogenesis and Valvulogenesis. Scientific reports 2016; 6:19459; Truong T, Huang E, Yuen D, Chen L. Corneal lymphatic valve formation in relation to 320 lymphangiogenesis. Investigative ophthalmology & visual science 2014; 55:1876-1883.) It is yet to be determined whether an intervention of the formation of these lymphatic valves, or valvulogenesis (VG), can modulate transplant survival, which is a focus of this study.

Itga-9 belongs to the integrin family that mediates cell-cell and cell-matrix interactions. Previously, it was reported that this molecule is highly expressed on newly formed lymphatic valves in the cornea, and its gene knockdown can inhibit the functions of human dermal lymphatic endothelial cells in vitro, such as proliferation, adhesion, migration, and tube formation. It was demonstrated with a suture placement model that Itga-9 blockade can suppress inflammatory VG in a brief two week study. (Altiok E, Ecoiffier T, Sessa R, et al. Integrin Alpha-9 Mediates Lymphatic Valve Formation in Corneal Lymphangiogenesis. Investigative ophthalmology & visual science 2015; 56:6313-6319). These preliminary results indicate a perfect opportunity to elucidate (1) whether Itga-9 blockade can be used as a new strategy to interfere with VG and/or LG induced by transplantation, which is a much more complicated procedure than inflammation. Transplantation triggers immune responses against foreign antigens and a greater degree of VG and LG; (2) whether VG plays a critical role in transplant rejection. To date, there has been no report on this aspect; and (3) whether Itga-9 blockade can be used to improve the outcomes of transplants. The current regimens of corticosteroids are of limited efficacy and also associated with many side effects, such as opportunistic infection, glaucoma and cataract. Lymphatic specific targeting may offer a more precise approach to promote graft survival. Therefore, results from this study may not only offer new insights into transplantation immunity but also provide a novel strategy to treat transplant rejection, and possibly other lymphatic- and immune-related diseases.

Methods

Animals

Six- to eight-week-old male BALB/c and C57BL/6 mice (Taconic Farms, Germantown, N.Y.) were used in the experiments, and mice were anesthetized using a mixture of ketamine, xylazine, and acepromazine (50 mg, 10 mg, and 1 mg/kg body weight, respectively) for each surgical procedure. All mice were treated according to the ARVO Statement for the Use of Animals in Ophthalmic and Vision Research and all protocols were approved by the Animal Care and Use Committee, University of California, Berkeley.

Corneal Transplantation

Orthotopic corneal transplantation was performed between fully mismatched C57BL/6 (donors) and BALB/c (recipients), as reported previously. (Zhang H, Grimaldo S, Yuen D, Chen L. Combined blockade of VEGFR-3 and VLA-1 markedly promotes high-risk corneal transplant survival. Investigative ophthalmology & visual science 2011; 52:6529-6535; Kang G J, Ecoiffier T, Truong T, et al. Intravital Imaging Reveals Dynamics of Lymphangiogenesis and Valvulogenesis. Scientific reports 2016; 6:19459 Basically, donor central cornea was marked with a 2 mm diameter micro-curette (Katena Products Inc., Denville, N.J.) and excised with Vannas scissors (Storz Instruments Co, San Dimas, Calif.). The recipient graft bed was similarly prepared with a 1.5 mm diameter micro-curette and the donor button was secured in recipient bed with eight interrupted 11-0 nylon sutures (Sharpoint; Vanguard). Antibiotic ointment was applied at the end of the surgery.

Pharmaceutical Intervention

The recipient mice were randomized to receive subconjunctival injections of either hamster or mouse Itga-9 antibody (6.4 µg; kindly provided by Dr. Toshimitsu Uede, Hokkaido University) or its isotype control hamster IgG (Jackson ImmunoResearch, West Grove, Pa., USA), as reported previously. 11 Subconjunctival injection was performed twice a week on the day of transplantation and thereafter up to 8 weeks after the surgery.

In Vivo Assessment of Grafted Corneas

After the transplantation surgery, all eyes were first examined on day 3 and corneal sutures were removed on day 7. Grafts were evaluated by ophthalmic slit-lamp biomicroscopy twice a week for 8 weeks according to the standard scheme. Basically, the degree of graft opacification was graded between 0 (clear and compact graft) to 5+(maximal opacity with total obscuration of the anterior chamber). Grafts with an opacity score of 2+ or higher after 3 weeks or an opacity score of 3+ or higher at 2 weeks were regarded as rejected.

Corneal Immunofluorescent Microscopy

The experiment was performed as described previously. (Truong T, Altiok E, Yuen D, Ecoiffier T, Chen L. Novel characterization of lymphatic valve formation during corneal inflammation. PloS one 2011; 6:e21918; Kang G J, Ecoiffier T, Truong T, et al. Intravital Imaging Reveals Dynamics of 318 Lymphangiogenesis and Valvulogenesis. Scientific reports 2016; 6:19459; Truong T, Huang E, Yuen D, Chen L. Corneal lymphatic valve formation in relation to lymphangiogenesis. Investigative ophthalmology & visual science 2014; 55:1876-1883) Briefly, whole-mount full thickness corneas were harvested at 8 weeks after transplantation and fixed in acetone for immunofluorescent staining. Samples were sequentially incubated with purified rabbit-mouse LYVE-1 (Abcam, Cambridge, Mass.) antibody and goat-anti-mouse Itga-9 antibody (R&D Systems, Minneapolis, Minn.), which were visualized by FITC-conjugated donkey-anti-rabbit and Cy3-conjugated donkey-anti-goat secondary antibodies (Jackson ImmunoResearch Laboratories, West Grove, Pa.), respectively. Samples were covered with Vector Shield mounting medium (Vector Laboratories, Burlingame, Calif.) and examined by an AxioImager M1 epifluorescence deconvolution microscope with AxioVision 4.8 software (Carl Zeiss AG, Göttingen, Germany).

Lymphatic Vessel and Valve Quantification

The analysis was performed as reported previously. (Truong T, Huang E, Yuen D, Chen L. Corneal lymphatic valve formation in relation to lymphangiogenesis. Investigative ophthalmology & visual science 2014; 55:1876-1883; Altiok E, Ecoiffier T, Sessa R, et al. Integrin Alpha-9 Mediates Lymphatic Valve Formation in Corneal Lymphangiogenesis. Investigative ophthalmology & visual science 2015; 56:6313-6319; Cursiefen C, Chen L, Borges L P, et al. VEGF-A stimulates lymphangiogenesis and hemangiogenesis in inflammatory neovascularization via macrophage recruitment. The Journal of clinical investigation 2004; 113:1040-1050; Schneider C A, Rasband W S, Eliceiri K W. NIH Image to ImageJ: 25 years of image analysis. Nature methods 2012; 9:671-675; Yuen D, Grimaldo S, Sessa R, et al. Role of angiopoietin-2 in corneal lymphangiogenesis. Investigative ophthalmology & visual science 2014; 55:3320-3327) Briefly, for LG evaluation, LYVE-1+ vascular structures were analyzed by NIH ImageJ software. (Truong T, Huang E, Yuen D, Chen L. Corneal lymphatic valve formation in relation to lymphangiogenesis. Investigative ophthalmology & visual science 2014; 55:1876-1883; Cursiefen C, Chen L, Borges L P, et al. VEGF-A stimulates lymphangiogenesis and hemangiogenesis in inflammatory neovascularization via macrophage recruitment. The Journal of clinical investigation 2004; 113:1040-1050; Schneider C A, Rasband W S, Eliceiri K W. NIH Image to ImageJ: 25 years of image analysis. Nature methods 2012; 9:671-675) The lymphatic invasion area was normalized to the total corneal area to obtain a percentage coverage score for each sample.

The total corneal area was measured by outlining the innermost lymphatic vessels of the limbal arcade, and lymphatic invasion area was determined by tracing out the contours of the LYVE-1+ lymphatic network inside the cornea. Additionally, the cornea was divided into four equal quadrants in reference to the vertical midline passing through the 6- and 12-o'clock positions, and the nasal and temporal quadrants were used for analysis of polarized lymphatic vessel distribution for each sample. Luminal valves were also evaluated and focal Itga-9+/LYVE-1− areas running along the length of the LYVE-1+ vessels were identified as valves and quantified for each sample. The percentage scores were obtained by normalizing to the means of control condition that were defined as being 100%.

Statistical Analysis

Data are expressed as mean+SEM. Mann-Whitney U test was used to evaluate the statistical significance of the difference between the groups. Corneal graft survival was assessed by Kaplan-Meier survival curves. The association analysis was performed by the linear mixed model built with R Studio platform (R Studio Inc., Boston, Mass.) using the nlme R package. All other statistical analysis was performed with Prism software (GraphPad, La Jolla, Calif.). $P<0.05$ was considered significant.

Results

Figure 1B:
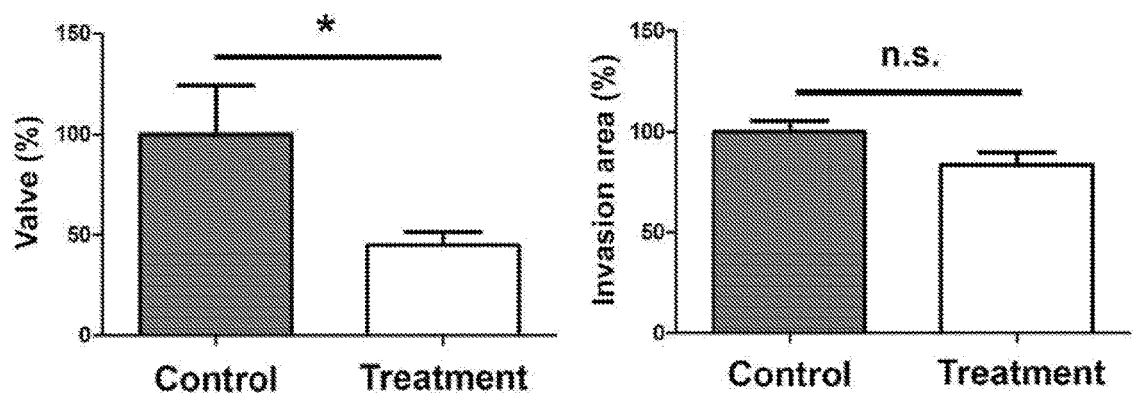
Figure 1C:
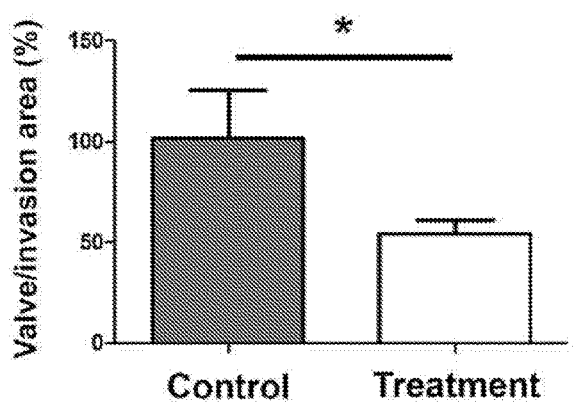

Effect of Itga-9 Blockade on Lymphatic Valvulogenesis after Corneal Transplantation The effect of Itga-9 blockade on corneal LG and VG induced by transplantation was first studied. Either Itga-9 neutralizing body or isotype control was injected subconjunctivally twice a week starting from the surgery date. As demonstrated in FIG. 1A, following the treatment with the Itga-9 blocking antibody, corneal lymphatic vessels contained significantly fewer valves compared with the control condition. Summarized data from repetitive experiments are presented in FIG. 1B (left panel; $P<0.05$). However, this treatment had no effect on LG, as shown in FIG. 1B (right panel). Further analysis on the ratio of valve quantity to lymphatic invasion area revealed a significant reduction in this parameter in the treated than the control condition (FIG. 1C; $P<0.05$).

Effect of Itga-9 Blockade on Nasal Dominant Distribution of Lymphatic Vessels

Figure 2A:
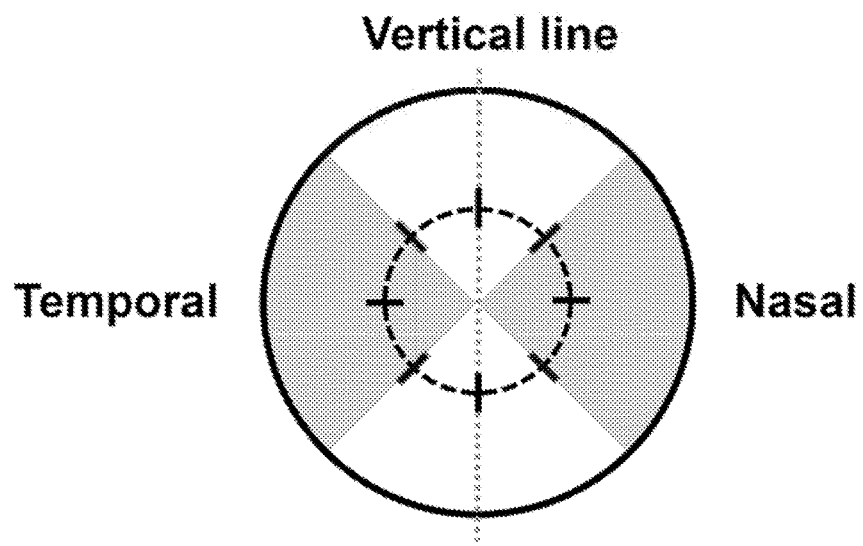
FIGS. 2A-2B. Itga-9 blockade had no effect on polarized distribution of lymphatic vessels after corneal transplantation.
Figure 2B:
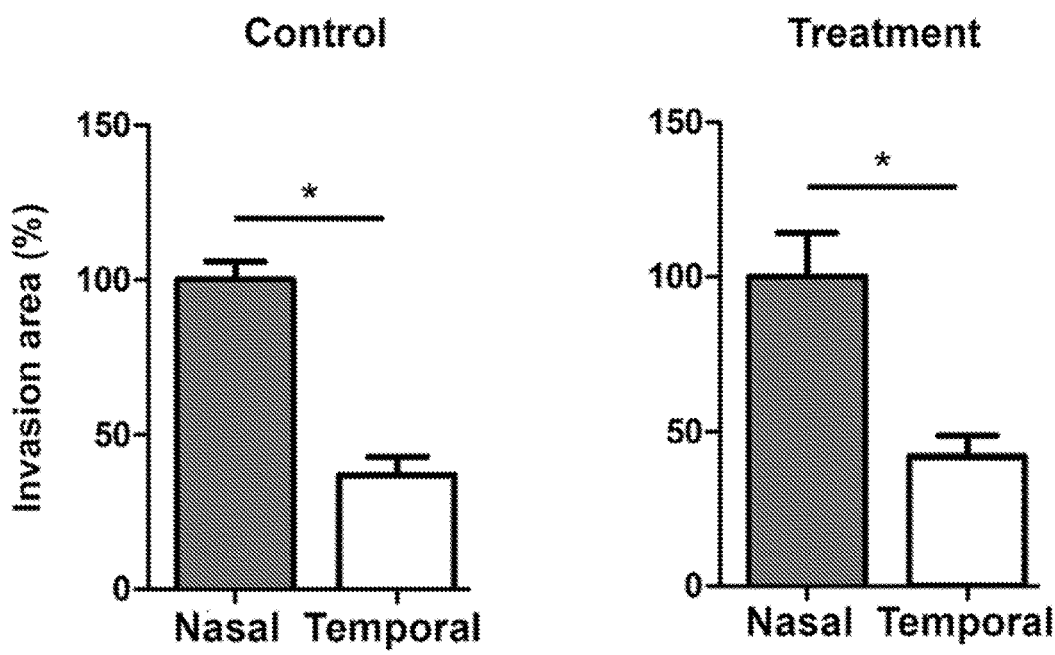
Figure 4:
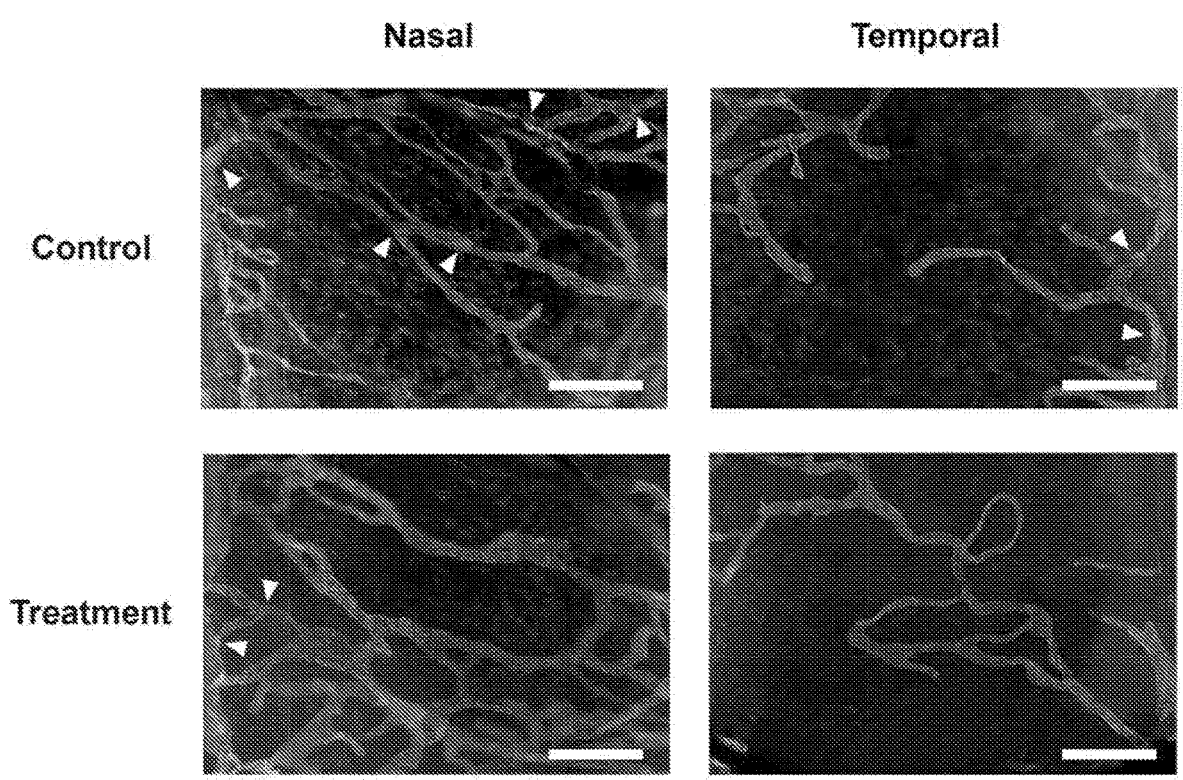
FIG. 4. Itga-9 blockade had no effect on this polarity of corneal LG.

Previously, it was reported that corneal lymphatic vessels observe a unique nasal dominant distribution pattern in inflammatory LG. (Truong T, Huang E, Yuen D, Chen L. Corneal lymphatic valve formation in relation to lymphangiogenesis. Investigative ophthalmology & visual science 2014; 55:1876-1883; Ecoiffier T, Yuen D, Chen L. Differential distribution of blood and lymphatic vessels in the murine cornea. Investigative ophthalmology & visual science 2010; 51:2436-2440) To investigate whether this phenomenon also manifests in transplantation-associated LG and whether it is affected by the Itga-9 treatment, the effect of Itga-9 blockade on the polarity of LG was next investigated by comparing the nasal and temporal quadrants, as illustrated in FIG. 2A. The results showed that in both treatment and control groups, lymphatic vessels were more distributed at the nasal side, and Itga-9 blockade had no effect on this polarity of corneal LG (FIG. 2B and FIG. 4). Further association analysis using the linear mixed model built with R Studio platform (R Studio Inc., Boston, Mass.) also confirmed that the polarized distribution of LG was only associated with corneal regions but not with the anti-Itga-9 blockade.

Effect of Itga-9 Blockade on Corneal Graft Survival

Figure 3A:
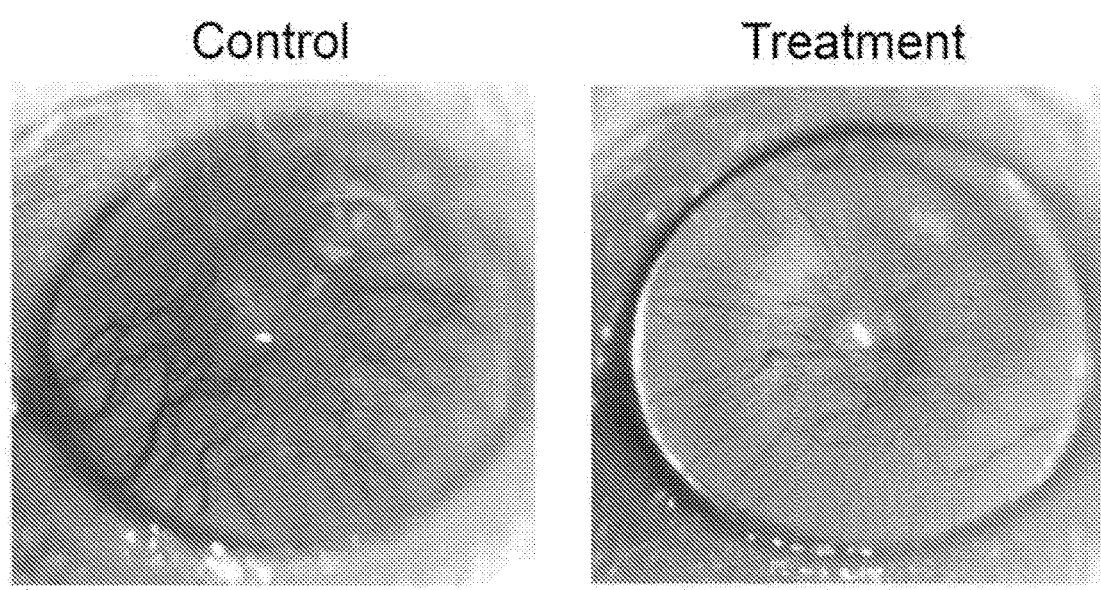
FIGS. 3A-3B. Itga-9 blockade promoted corneal graft survival.
Figure 3B:
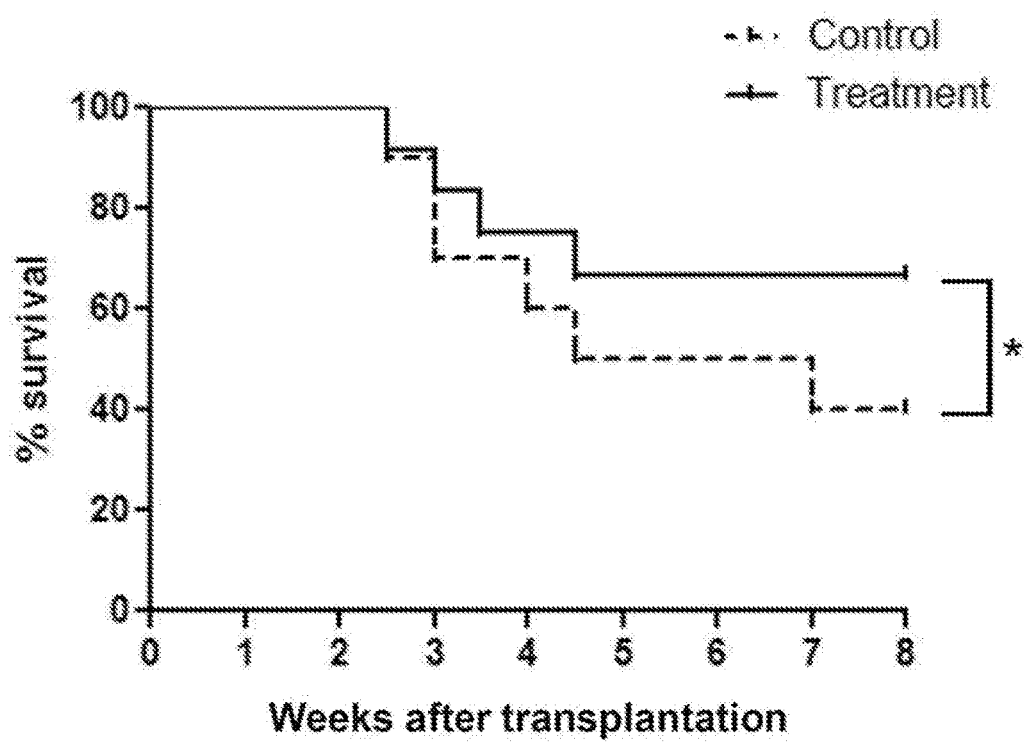

To further evaluate the effect of Itga-9 blockade on corneal graft survival, the grafts were examined in both treatment and control groups and evaluated their survival rate twice a week up to 8 weeks after the surgery. As shown in FIG. 3, the results showed a significant promotion of graft survival by this treatment. While graft rejection in both the control and treatment group started around 2.5 weeks after transplantation, significantly higher percentage of the grafts survived in treatment group by the end of the 8-week study, as analyzed by the Kaplan-Meier survival curves ($P<0.05$).

Discussion

In this study, it was demonstrated for the first time that Itga-9 is critically involved in corneal transplantation-induced VG, and its molecular blockade can effectively suppress this process. It has also been shown that this treatment strategy does not affect corneal LG or its polarity of nasal distribution. More important, the first evidence is offered showing that by reducing the lymphatic valves but not the vessels themselves, it was possible to achieve a higher rate of graft survival.

Figure 5:
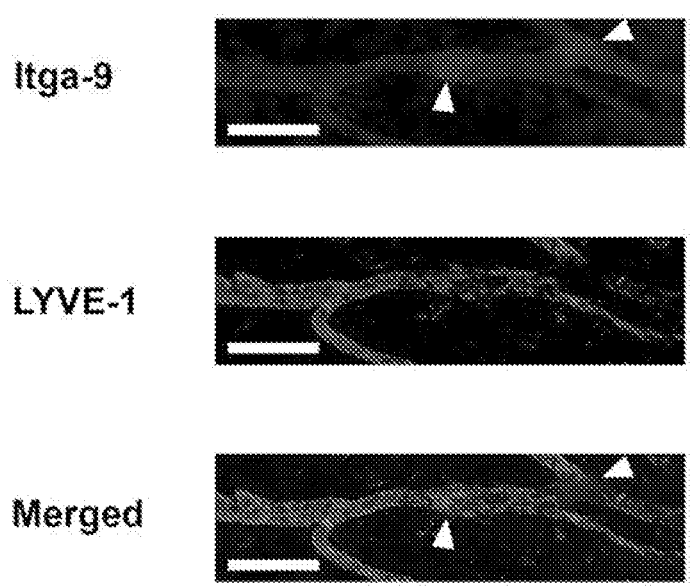
FIG. 5. Itga-9 is more highly expressed on the valves than the vessel walls.

The finding that Itga-9 blockade suppressed lymphatic valve formation without disturbing the lymphatic vessels in transplantation is consistent with a previous report on a suture-induced inflammation model. (Altiok E, Ecoiffier T, Sessa R, et al. 323 Integrin Alpha-9 Mediates Lymphatic Valve Formation in Corneal Lymphangiogenesis. Investigative ophthalmology & visual science 2015; 56:6313-6319) It seems that lymphatic valves are more responsive to Itga-9 intervention than lymphatic vessels. This may be explained by the fact that Itga-9 is more highly expressed on the valves than the vessel walls (FIG. 5). The disparity between lymphatic valves and vessels was also observed during development where reduced number of lymphatic valves, but not vessels, were detected in Itga-9 knockout mice. (Bazigou E, Xie S, Chen C, et al. Integrin-alpha9 is required for fibronectin matrix assembly during lymphatic valve morphogenesis. Developmental cell 2009; 17:175-186.) With the treatment regimen used in this study, no obvious side effects were observed.

It is remarkable that prevention of lymphatic valve formation can significantly increase graft survival. This finding indicates a compromise of the immune reflex arm where the lymphatic pathway serves as the afferent arm. It also aligns well with a previous developmental report that Itga-9 knockout mice died shortly after birth from bilateral chylothorax where lymphatic vessels were present but displayed compromised integrity. (Huang X Z, Wu J F, Ferrando R, et al. Fatal bilateral chylothorax in mice lacking the integrin alpha9beta1. Molecular and cellular biology 2000; 20:5208-5215.) Moreover, lymphatic vessels are equipped with valves as they become mature and functional. Therefore, by targeting on lymphatic valves, the maturation process of the lymphatic vessels may have been interfered with, rendering them dysfunctional.

In summary, this study reveals an important role of lymphatic VG in mediating transplant rejection. It also provides a novel therapeutic strategy to effectively interfere with this pathological process and to improve graft survival. The results from the cornea may shed some light on the development of new Itga-9-based therapies to treat broader lymphatic and immune diseases in body.

Example 2

Figures 6A, 6B:
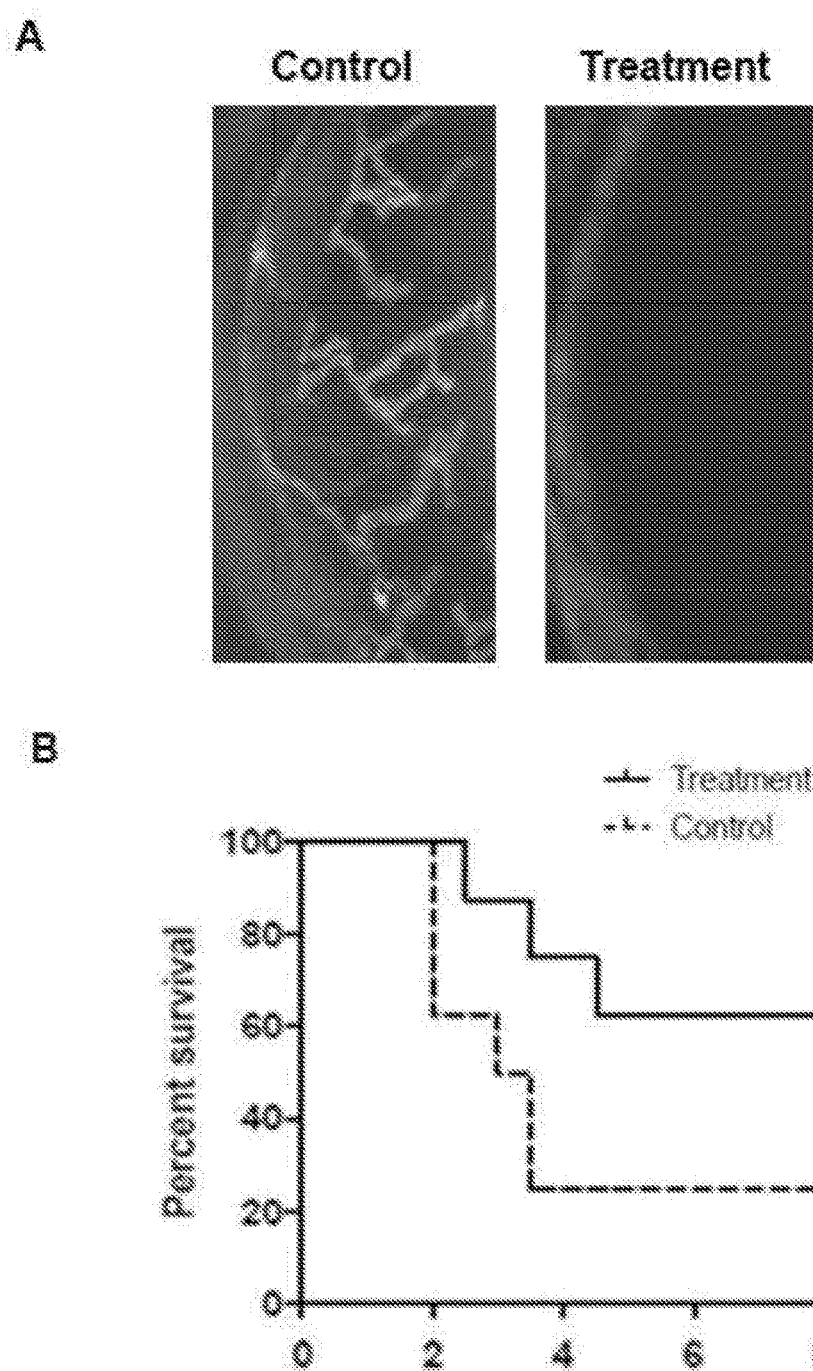
FIGS. 6A and 6B. Combined blockade of ltga-9 and VEGFR-3 inhibits lymphatic valve and vessel formation after high-risk corneal transplantation (FIG. 6, vessels and valves shown in green color) and promotes graft survival (FIG. 6B, Kaplan-Meier survival curve).

Further studies showed that a combined blockade of Itga-9 and VEGFR-3 inhibits lymphatic valve and vessel formation after high-risk corneal transplantation (FIG. 6, vessels and valves shown in green color) and promotes graft survival (FIG. 6B, Kaplan-Meier survival curve).

Example 3

PURPOSE. We recently reported that corneal lymphatic vessels develop integrin alpha-9 (Itga-9)-positive valves during inflammatory lymphangiogenesis. The purpose of this study was to further investigate the role of Itga-9 in corneal lymphatic valve formation in vivo and lymphatic endothelial cell (LEC) functions in vitro.

METHODS. Standard murine suture placement model was used to study the effect of Itga-9 blockade on lymphatic valve formation in vivo using Itga-9 neutralizing antibody. Wholemount corneas were harvested for immunofluorescent microscopic analysis. Additionally, human skin LEC culture system was used to examine the effect of Itga-9 gene knockdown on cell functions using small interfering RNAs (siRNAs).

RESULTS. Itga-9 blockade in vivo significantly reduced the number of lymphatic valves formed in the inflamed cornea. Moreover, Itga-9 gene knockdown in human LECs suppresses cell functions of proliferation, adhesion, migration, and tube formation.

CONCLUSIONS. Itga-9 is critically involved in corneal lymphatic valve formation. Further investigation of the Itga-9 pathway may provide novel strategies to treat lymphatic-related diseases occurring both inside and outside the eye.

Introduction

The lymphatic network permeates most tissues and plays important functions in tissue fluid homeostasis and immune surveillance. A broad spectrum of diseases and conditions are associated with lymphatic dysfunction including inflammation, cancer metastasis, and transplant rejection.[1-5] Despite the prevalence of diseases associated with the lymphatic system, there are still few treatments available for lymphatic disorders. It is therefore a field with an urgent demand for new therapeutic strategies.

With the discovery of several lymphatic-specific markers, such as lymphatic vessel endothelial hyaluronan receptor-1 (LYVE-1) and transcription factor prospero homeobox protein-1 (Prox-1), the field of lymphatic research has expanded rapidly in the last decade.[6,7] There is increasing evidence pointing to the role of integrins in the lymphatic system though it is yet to be fully investigated.[8] Integrins are a family of heterodimeric cell surface transmembrane glycoproteins involved in cell-cell and cell-matrix interactions.[9-11] Several studies from us and other researchers have shown that integrin a5b1, a1b1, and a4b1 mediate inflammation- or tumor-associated lymphangiogenesis (LG, the formation of new lymphatic vessels).[12-15] More recently, we have reported that corneal lymphatic vessels develop luminal valves as inflammatory LG proceeds, and these valves, consisting of endothelial layers, express integrin a9b1 (Itga-9), and function to direct lymph flow in inflamed corneas.[16,17] However, the direct role of Itga-9 in corneal lymphatic valve formation and lymphatic endothelial cell (LEC) function still remain to be elucidated, which is the focus of this study. Answers to these questions are essential for developing new therapeutic strategies for lymphatic diseases.

In this paper, using in vivo murine model of corneal inflammatory LG with valve formation and in vitro human LEC culture system, we provide the first evidence showing that Itga-9 is critically involved in corneal lymphatic valve formation in vivo and LEC functions in vitro. Itga-9 blockade in vivo via neutralizing antibodies significantly suppresses lymphatic valve formation in inflamed cornea. Additionally, Itga-9 depletion in LECs via small interfering RNAs (siRNAs) halts critical cellular processes in vitro, such as proliferation, adhesion, migration, and tube formation. Taken together, this work reveals a critical role of Itga-9 in corneal lymphatic valve formation. The combined in vivo animal work and in vitro human cell research should provide highly translational information for future development of new therapeutic strategies to treat lymphatic disorders that occur both inside and outside the eye.

Methods

Animals

Six- to 8-week-old normal adult male BALB/c mice were purchased from Taconic Farms (Germantown, N.Y., USA). All mice were treated according to ARVO Statement for the Use of Animals in Ophthalmic and Vision Research and the protocols approved by the Animal Care and Use Committee of the institute. Mice were anesthetized using a mixture of ketamine, xylazine, and acepromazine (50-, 10-, and 1-mg/kg body weight, respectively) for each surgical procedure.

Induction of Corneal Lymphangiogenesis and Administration of Blocking Antibody

The suture placement model was used to induce corneal inflammatory LG with valve formation, as previously described.[16] Briefly, three 11-0 nylon sutures (AROSurgical, Newport Beach, Calif., USA) were placed into the corneal stroma without penetrating into the anterior chamber. Subsequently, mice were randomized to receive subconjunctival injections of either 6.4 lg hamster anti-mouse Itga-9 blocking antibody[18] or isotype control hamster IgG (Jackson ImmunoResearch, West Grove, Pa., USA) twice a week for 2 weeks beginning on day 0 after suturing. Experiments were repeated twice with a total of 10 mice in each group.

Immunofluorescent Microscopic Assay and Lymphatic Valve Quantification

The experiments were performed as previously reported.[16,19] Briefly, whole-mount corneas were fixed in acetone for immunofluorescent staining. Samples were sequentially incubated with purified rabbit-anti-mouse LYVE-1 (Abcam, Cambridge, Mass., USA) and goat-anti-mouse Itga-9 antibodies (R&D Systems, Minneapolis, Minn., USA), which were visualized by FITCconjugated donkey-anti-rabbit and Cy3-conjugated donkey-antigoat secondary antibodies (Jackson ImmunoResearch), respectively. Samples were mounted with Vector Shield mounting medium (Vector Laboratories; Burlingame, Calif., USA) and examined using a Zeiss LSM 710 AxioObserver Inverted Confocal microscope with ZEN Digital Imaging software (Carl Zeiss, Inc., (Germany). Itga-9Þ focal areas along the length of LYVE-1Þ lymphatic vessels were identified as valves. The number of lymphatic valves per cornea was quantified and the percentage scores were obtained by normalizing to control groups where the scores were defined as being 100%.[16,19]

Lymphatic Endothelial Cell Culture and Immunocytofluorescent Microscopic Assay

The experiments were performed as previously described.[13,19] Briefly, human neonatal microdermal LECs were purchased from Lonza (Walkersville, Md., USA) and maintained in EGM-2MV cell culture medium (Lonza) according to manufacturer's instructions. For LEC staining, cells were incubated with rabbit anti-human-Itga-9 antibody (Novus Biologicals, Littleton, Colo., USA) and visualized by Cy3-conjugated donkey-anti-rabbit secondary antibody (Jackson ImmunoResearch). Samples were mounted with DAPI mounting medium (Vectashield; Vector Laboratories). Digital images were taken with a Zeiss Axioplan 2 epifluorescence microscope (Carl Zeiss, Inc.).

siRNA Transfection

The experiments were performed as previously reported.[13,19] Custom-designed siRNA duplexes were synthesized by Qiagen (Valencia, Calif., USA) against human Itga-9 mRNA (50-AAG AAG AAA GTC GTA CTA TAG-30 (SEQ ID NO: 1)). Scrambled siRNA control was purchased from Ambion (Austin, Tex., USA). Transfections were carried out according to manufacturer's instructions with a transfection reagent (RNAiMax; Invitrogen, Carlsbad, Calif., USA) and opti-MEM-reduced serum medium at 378 C in a 5% $CO_2$ humidified air incubator.

Reverse Transcription and Real-Time PCR

The experiments were performed as previously described and based on the minimum information for publication of quantitative real-time PCR experiments (MIQE) guidelines.[13,19,20] Total RNA was extracted and purified from LECs 48 hours after siRNA transfection with an RNAeasy mini-kit from Qiagen. Reverse transcription was performed using the SuperScript VILO cDNA synthesis kit from Invitrogen. Primer sequences were as follows: human Itga-9, forward 50-CGG AAT CAT GTC TCC AAC CT-30 (SEQ ID NO: 2) and 50-TCT CTG CAC CAC CAG ATG AG-30 (SEQ ID NO: 3); human b-actin, forward 50-GAT CTG GCA CCA CAC CTT CT-30 (SEQ ID NO: 4), reverse 50-GGG GTG TTG AAG GTC TCA AA-3.0 (SEQ ID NO: 5) Realtime PCR was performed using SsoFast EvaGreen with the CFX96 sequence detection system (Bio-Rad Laboratories, Inc., Hercules, Calif., USA). Relative expression of the Itga-9 gene was calculated from the D-Ct (threshold cycle) of the targeted gene normalized to the D-Ct of actin.

Flow Cytometry

Forty-eight hours after LEC transfection, LEC viability was evaluated by Guava ViaCount assay (Millipore, Billerica, Mass., USA). Data were acquired using a Guava easyCyte HT cytometer (Millipore) and the InCyte 2.6 software (Millipore). Viable and nonviable cells were assessed by the differential permeability of two DNA-binding dyes in the Guava ViaCount reagent. One dye stains all nucleated cells (red fluorescent channel), while the other dye stains nonviable cells (yellow fluorescent channel). Live cells were gated (R1) and the percentage over the total population was calculated. Experiments were repeated three times and the percentage scores were normalized to the control condition where the scores were defined as being 100%.

Proliferation Assay

As described previously,[13,19] LECs were seeded into 96-well plates. Forty-eight hours following siRNA transfection with either Itga-9 or scrambled siRNA, cells were subjected to a MTS proliferation assay from Promega (Madison, Wis., USA) according to the manufacturer's protocol. Assays were performed in triplicate and repeated three times.

Adhesion Assay

As described previously, 13 forty-eight hours following siRNA transfection with either Itga-9 or scrambled siRNA, LECs were seeded into 96-well plates coated with fibronectin. Plates were incubated for 1 hour at 378 C, washed twice and incubated with calcein (1 lg/mL) in HBSS for 30 minutes at room temperature. Plates were washed with PBS and fluorescence intensity was measured with a microplate reader (Spectramax M5e; Molecular Devices, Sunnyvale, Calif., USA). Assays were performed in triplicate and repeated three times.

Migration Assay

Forty-eight hours following siRNA transfection with either Itga-9 or scrambled siRNA, a 10-1L pipette tip was used to createlinear wounds within LEC monolayers. Differential interference contrast (DIC) phase images were taken at 0, 24, and 72 hours post scratch to visualize wound closure in cell monolayers. Scratches were analyzed for wound healing using the TScratchprogram (Tobias Gebäck and Martin Schulz, ETH Zürich). Cells were stained using TRITC-conjugated phalloidin (Millipore, Temecula, Calif., USA) for visualization of cell migration during wound closure.

Tube Formation Assay

As described previously, 13,19 48 hours following siRNA transfection with either Itga-9 or scrambled siRNA, LECs were seeded (2 3 $10^4$ cells/well) onto 96-well plates containing solidified Matrigel (BD Biosciences, San Jose, Calif., USA). Tube formation was imaged at 24 hours post seeding using a Zeiss Axio Observer Al inverted microscope (Carl Zeiss, Inc.). Phase images of tubes were taken (Qcapture; Qimaging, Surrey, BC, Canada) and total tube length per well was calculated using ImageJ software (http://imagej.nih.gov/ij/; provided in the public domain by the National Institutes of Health, Bethesda, Md., USA). Assays were performed in triplicate and repeated at least three times.

Statistical Analysis

The results are reported as mean 6 SEM and Student t-test was used for the determination of significance levels between different groups using Prism software (GraphPad, La Jolla, Calif., USA). The differences were considered statistically significant when $P<0.05$.

Results

Effect of Itga-9 Blockade on Corneal Lymphatic Valve Formation In Vivo

Figures 7A, 7B:
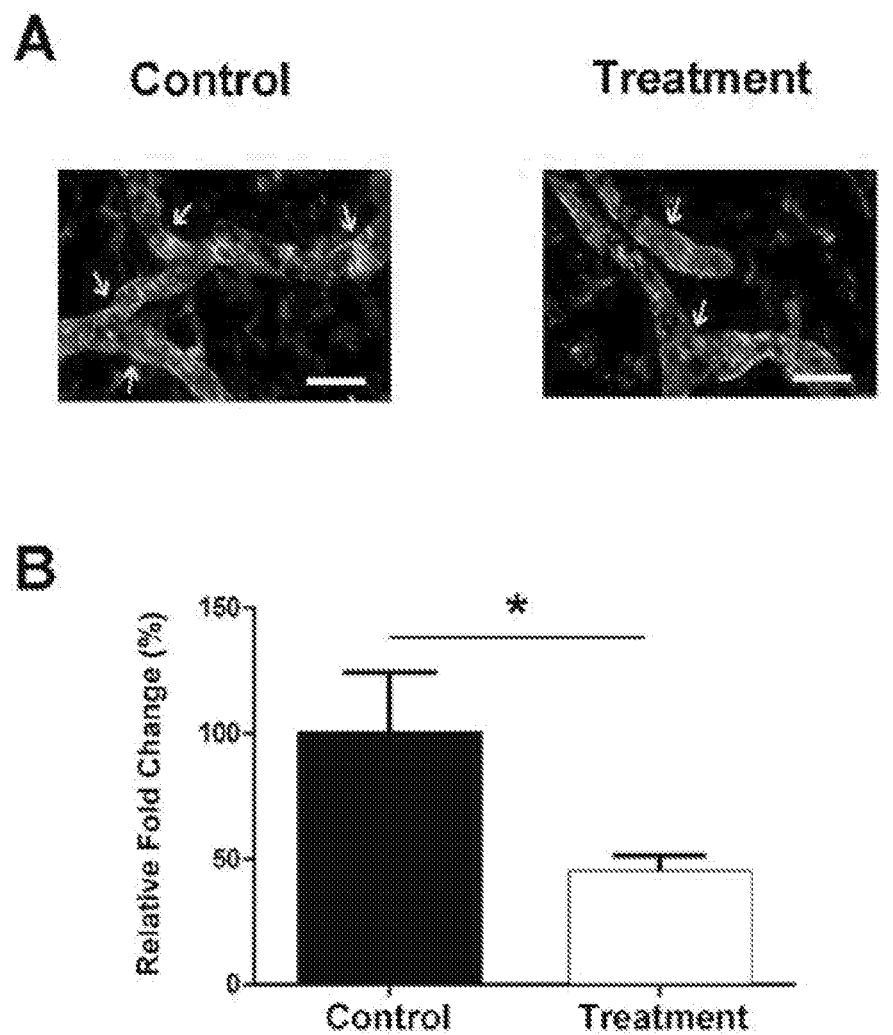
FIGS. 7A and 7B. Itga-9 blockade inhibits corneal valve formation in vivo.

We first set out to study the effect of Itga-9 blockade on corneal lymphatic valve formation in inflammatory LG. The standard suture placement model was used to evaluate the effect of subconjunctival delivery of Itga-9 neutralizing antibody on the number of valves formed in inflamed corneas with LG. As presented in FIG. 7A, following treatment with the Itga-9 blocking antibody, corneal lymphatic vessels contained significantly fewer valves compared with the control condition. Summarized data from repetitive experiments are shown in FIG. 7B (*$P<0.05$).

Itga-9 Expression and Depletion in LECs

Figures 8A, 8B:
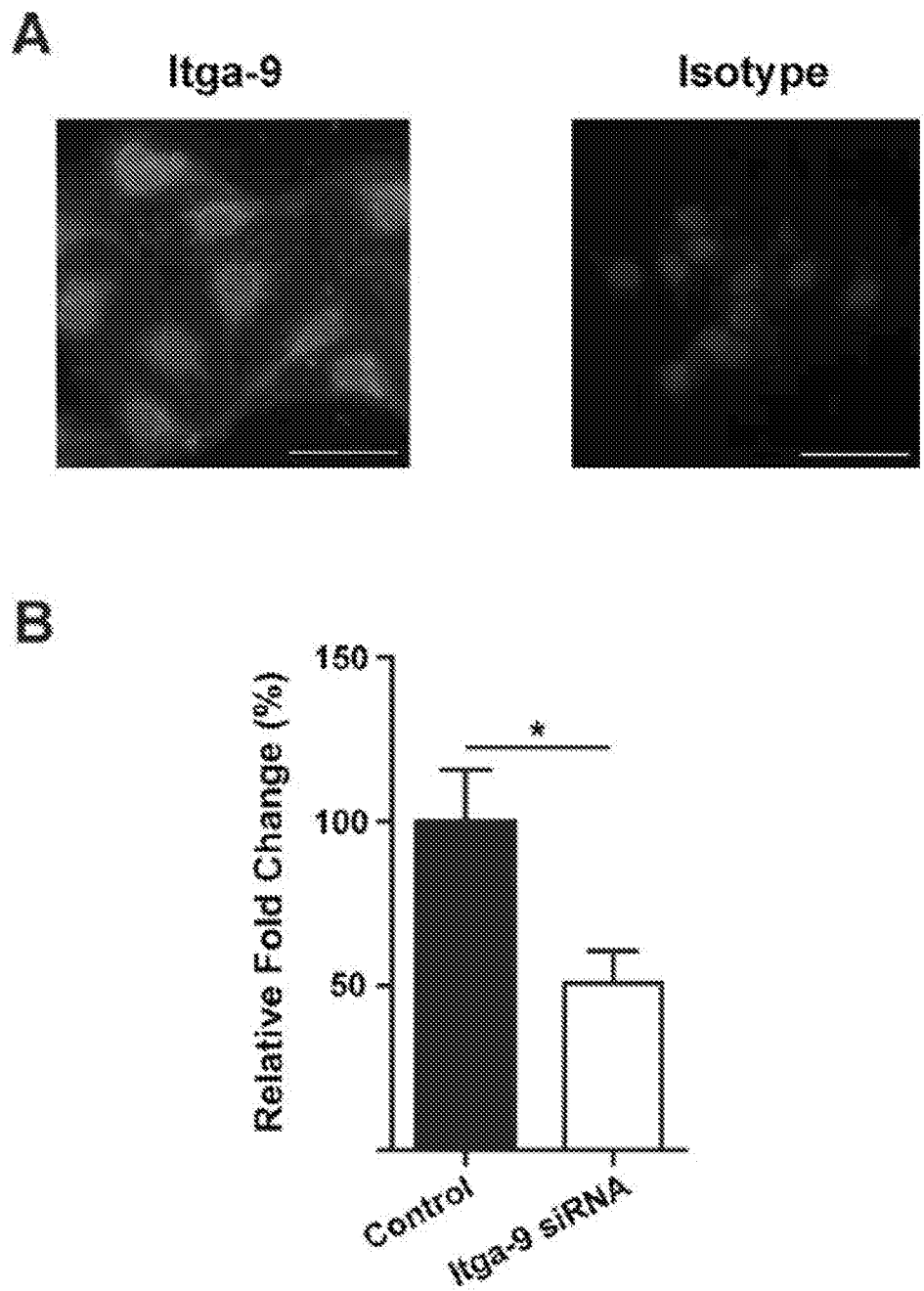
FIGS. 8A and 8B. Expression and depletion of Itga-9 in human skin LECs.
Figure 9:
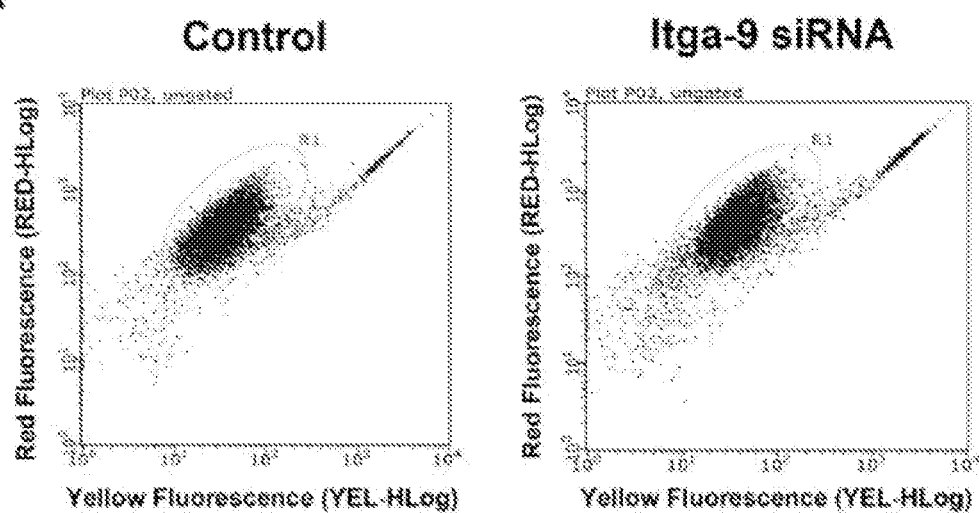
FIGS. 9A and 9B. Itga-9 knockdown has no effect on LEC viability.
Figure 9:
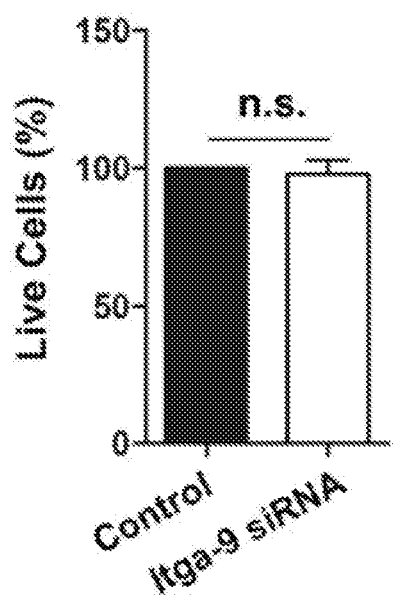

Lymphatic valves are made of the extracellular matrix sandwiched by two layers of endothelial cells. To further investigate the specific role of Itga-9 in lymphatic endothelial cells in vitro, we next employed the human LEC culture system. As shown in FIG. 8A, we first confirmed the expression of Itga-9 on these cells by the immunocytofluorescent microscopic analysis. We then assessed whether Itga-9 expression in these LECs can be downregulated by a siRNA mediated gene silencing approach (FIG. 8B). Our data from realtime PCR analysis showed that following the transfection with Itga-9 siRNA, the Itga-9 expression in LECs was significantly reduced by around 50%. We also confirmed that the transfection had no direct effect on LEC viability by flow cytometric analysis with the Guava ViaCount assay, as shown in FIG. 9. Together, these data indicate that transfection with siRNA can be used to study the functional role of Itga-9 in LECs in vitro.

Effect of Itga-9 Depletion on Proliferation of LECs

Figures 10A, 10B:
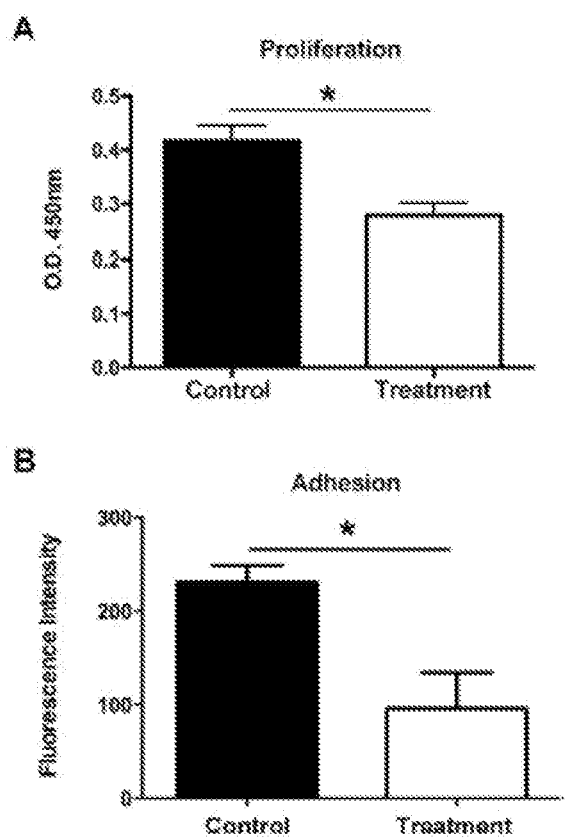
FIGS. 10A-10B. Itga-9 knockdown inhibits LEC functions of proliferation and adhesion.
Figure 11A:
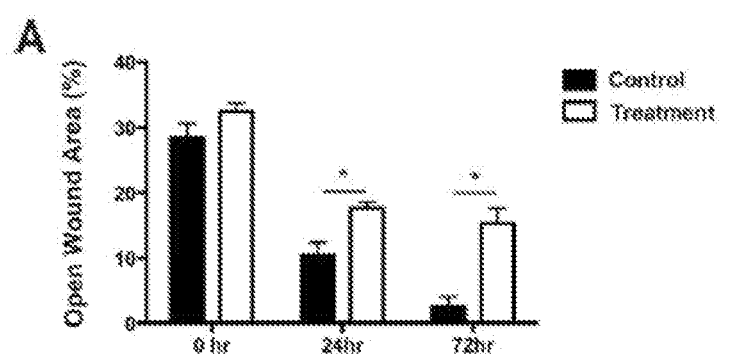
FIGS. 11A-11B. Itga-9 knockdown inhibits LEC migration.
Figure 11B:
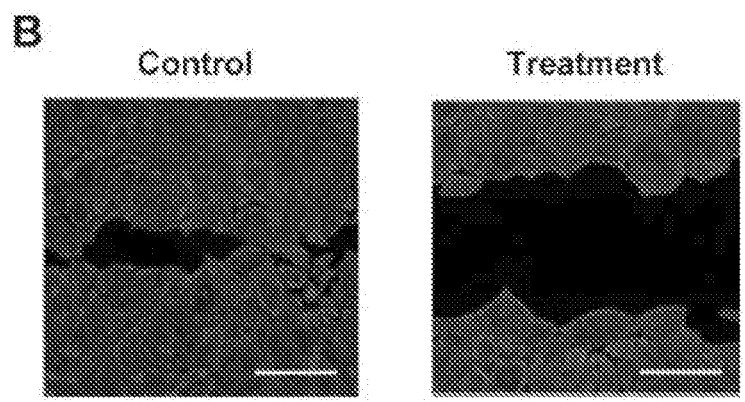

We next delved deeper and assessed the role of Itga-9 in the LEC function of proliferation using the siRNA approach. Fortyeight hours after siRNA transfection with either Itga-9 or scrambled siRNA, LECs were subjected to a MTS proliferation assay, as reported previously.[19] Our data, as presented in FIG. 10A, showed that Itga-9 siRNA treatment led to a significant reduction in LEC proliferation in comparison with control condition (*P<0.05). This result suggests that Itga-9 engagement regulates LEC proliferation. Effect of Itga-9 Depletion on Adhesion of LECs Integrins are essential for cellular adhesion to extracellular proteins. To investigate whether Itga-9 is important for LEC adhesion, cells were transfected with Itga-9 or scrambled siRNA and subjected to an adhesion assay on wells coated with Itga-9 ligand, fibronectin. As presented in FIG. 10B, Itga-9 depletion in LECs resulted in a significant reduction of cell adhesion to fibronectin (*P<0.05), indicating that Itga-9 is also crucial for LEC interaction with the extracellular matrix. Effect of Itga-9 Depletion on Migration of LECs Cell migration is a process mainly dependent on the interaction between integrins and extracellular matrix proteins, we next investigated the importance of Itga-9 on LEC migration using a scratch assay of wound healing. Following siRNA transfection with either Itga-9 or scrambled siRNA, LECs were monitored over 72 hours. As shown in FIG. 11A, LECs transfected with Itga-9 siRNA showed larger open wound area than control cells transfected with scramble siRNA at both time points studied, 24 and 72 hours after wounding (*P<0.05). Moreover, the inhibition effect of Itga-9 on wound healing was greater at the later time point when cells in the control group had grown over to majority of the field of view (FIG. 11B). These results clearly indicate that Itga-9 is essential for LEC migration.

Effect of Itga-9 Depletion on Tube Formation of LECs

Figure 12A:
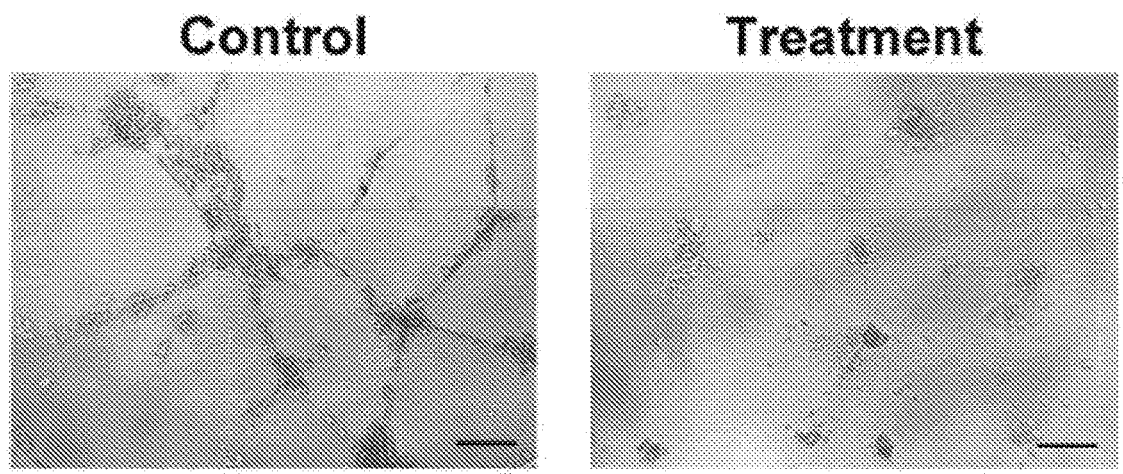
FIGS. 12A-12B. Itga-9 knockdown inhibits LEC tube formation.
Figure 12B:
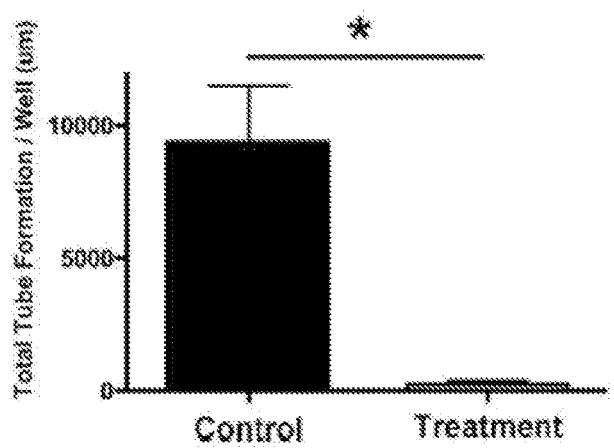

We also investigated the effect of Itga-9 depletion on the ability of LECs to organize into capillary-type tubes using a three dimensional culture system. Forty-eight hours after transfection with either Itga-9 or scramble siRNA, LECs were seeded on solidified basement membrane matrix, Matrigel, to allow for tube formation. Results from this assay showed that Itga-9 depletion in LECs resulted in a dramatic reduction in total tube length, as demonstrated in FIG. 12A. Summarized data from repetitive experiments are presented in FIG. 12B (*P<0.05). These results imply a critical role of Itga-9 in LEC organization into macroscale structures.

Discussion

In the present study, we have demonstrated the essential role of Itga-9 in corneal lymphatic valve formation and LECs using both in vivo animal and in vitro human cell models. We are able to draw two interdependent conclusions from this study. Firstly, lymphatic valve formation in vivo is tightly regulated by Itga-9, as shown through the experiments using Itga-9 blocking antibody. Secondly, Itga-9 is critically involved in LEC processes in vitro, such as proliferation, migration, and adhesion, as revealed by the siRNA knockdown approach. While the in vivo data suggest a new strategy to interfere with lymphatic valve formation in inflamed corneas, the in vitro results provide more details on possible mechanisms underlying the role of Itga-9 in various functions of LECs, which together orchestrate the process of valve formation. Cell anchorage to extracellular matrix is primarily mediated through integrin-based linkages, creating a strong connection between the intracellular and extracellular environments.[11] Integrins have specificity in extracellular matrix proteins depending on the a and b subunits. One of the main ligands for Itga-9 is fibronectin, as reported in a human cancer cell model. 21 In this study with human LECs, using Itga-9 targeting siRNA, we are able to show that upon depletion of Itga-9, LEC adhesion to fibronectin is significantly inhibited. Furthermore, at the core of cell migration are cell-matrix adhesion complexes, which are composed principally of integrins that link extracellular matrix to intracellular actin.[22] To identify the role of Itga-9 in LEC migration, we investigated the effect of Itga-9 loss on cell migration through a wound healing scratch assay. We are able to show that LECs lacking Itga-9 never fully migrates over the scratch wound in comparison to control LECs, which completely grows over the scratch surface over the course of time. Collectively with the proliferation data, the significance of Itga-9 in processes associated with LEC linkage to the extracellular matrix becomes unquestionable. Further investigation on these basic processes may divulge new targets for therapeutic intervention. Moreover, our in vitro data demonstrate that LECs with Itga-9 depletion lost their ability to form capillary type tubes in culture. However, our in vivo treatment regimen with the Itga-9 blocking antibody shows no significant reduction of lymphatic vessels but valves. Nevertheless, this discrepancy phenomenon is also observed in a previous study on lymphatic valve formation in nonocular tissues during development. Particularly, Bazigou et al.[23] examined lymphatic valve formation in Itga-9 knockout mice and reported reduced number of valves, but not lymphatic vessels, in Itga-9 homozygotes. One possible explanation for our in vivo data with the neutralizing antibody is that Itga-9 is more highly expressed on corneal lymphatic valves than vessels,[16,17] which may render the valves more sensitive to the anti-Itga-9 treatment. This warrants further investigation. Taken together, these results designate Itga-9 as an ideal target to manipulate lymphatic valve formation without disturbing the vessels. It is also suggested that a combined valve/vessel targeting approach is necessary when an intervention of both valves and vessels are required in disease management, which demands further research as well. Because the lymphatic vessels constitute the afferent arm of the immune reflex arc, 1 and their luminal valves function to direct lymph (containing immune cells) flow inside the vessels, it is speculated that by manipulating the number of vessels and/or valves formed inside the corneas, we could possibly interfere with the degree of the immune responses and the progression and resolution of the diseases at various stages. In summary, this study not only offers new insights into corneal valve formation but may also shed some light on future development of new Itga-9-based therapies for the broad spectrum of lymphatic diseases occurring inside or outside the eye.

Example 3 References

1. Chen L. Ocular lymphatics: state-of-the-art review. Lymphology. 2009; 42:66-76.
2. Christiansen A, Detmar M. Lymphangiogenesis and cancer. Genes Cancer. 2011; 2:1146-1158.
3. Alitalo K. The lymphatic vasculature in disease. Nat Med. 2011; 17:1371-1380.
4. Zhang H, Grimaldo S, Yuen D, Chen L. Combined blockade of VEGFR-3 and VLA-1 markedly promotes high-risk corneal transplant survival. Invest Ophthalmol Vis Sci. 2011; 52:6529-6535.
5. Dietrich T, Bock F, Yuen D, et al. Cutting edge: lymphatic vessels, not blood vessels, primarily mediate immune rejections after transplantation. J Immunol. 2010; 184: 535-539.
6. Banerji S, Ni, J, Wang, S X, et al. LYVE-1, a new homologue of the CD44 glycoprotein, is a lymph-specific receptor for hyaluronan. J Cell Biol. 1999; 144:789-801.
7. Wigle J T, Oliver, G. Prox1 function is required for the development of the murine lymphatic system. Cell. 1999; 98: 769-778.
8. Avraamides C J, Garmy-Susini B, Varner J A. Integrins in angiogenesis and lymphangiogenesis. Nat Rev Cancer. 2008; 8:604-617.
9. Berman A E, Kozlova N I, Morozevich G E. Integrins: structure and signaling. Biochemistry Biokhimiia. 2003; 68:1284-1299.
10. Stepp M A. Corneal integrins and their functions. Exp Eye Res. 2006; 83:3-15.
11. Giancotti F G. Integrin signaling. Science. 1999; 285: 1028-1033.
12. Dietrich T, Onderka J, Bock F, et al. Inhibition of inflammatory lymphangiogenesis by integrin a5 blockade. Am J Pathol. 2007; 171:361-372.
13. Grimaldo S, Yuen D, Ecoiffier T, Chen L. Very late antigen-1 mediates corneal lymphangiogenesis. Invest Ophthalmol Vis Sci. 2011; 52:4808-4812.
14. Garmy-Susini B, Makale M, Fuster M, Varner J A. Methods to study lymphatic vessel integrins. Methods Enzymol. 2007; 426: 415-438.
15. Chen L, Huq S, Gardner H, de Fougerolles A R, Barabino S, Dana M R. Very late antigen 1 blockade markedly promotes survival of corneal allografts. Arch Ophthalmol. 2007; 125: 783-788.
16. Truong T, Altiok E, Yuen D, Ecoiffier T, Chen L. Novel characterization of lymphatic valve formation during corneal inflammation. PloS One. 2011; 6:e21918.
17. Truong T, Huang E, Yuen D, Chen L. Corneal lymphatic valve formation in relation to lymphangiogenesis. Invest Ophthalmol Vis Sci. 2014; 55:1876-1883.
18. Kanayama M, Kurotaki D, Morimoto J, et al. Alpha9 integrin and its ligands constitute critical joint microenvironments for development of autoimmune arthritis. J Immunol. 2009; 182: 8015-8025.
19. Yuen D, Grimaldo S, Sessa R, et al. Role of angiopoietin-2 in corneal lymphangiogenesis. Invest Ophthalmol Vis Sci. 2014; 55:3320-3327.
20. Bustin S A, Benes V, Garson J A, et al. The MIQE guidelines: minimum information for publication of quantitative real-time PCR experiments. Clin Chem. 2009; 55:611-622.
21. Liao Y F, Gotwals P J, Koteliansky V E, Sheppard D, Van DeWater L. The EIIIA segment of fibronectin is a ligand for integrins alpha 9beta 1 and alpha 4beta 1 providing a novel mechanism for regulating cell adhesion by alternative splicing. J Biol Chem. 2002; 277:14467-14474.
22. Lock J G, Wehrle-Haller B, Stromblad S. Cell-matrix adhesion complexes: master control machinery of cell migration. Semin Cancer Biol. 2008; 18:65-76.
23. Bazigou E, Xie S, Chen C, et al. Integrin-alpha9 is required for fibronectin matrix assembly during lymphatic valve morphogenesis. Dev Cell. 2009; 17:175-186.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of inhibiting transplant rejection in a mammal in need thereof comprising administering an effective amount of a therapeutic agent to the mammal, wherein the therapeutic agent is an anti-Itga-9 therapeutic agent,
wherein a tissue for transplant comprises a cornea or skin,
wherein the anti-Itga-9 therapeutic agent comprises a binding agent specific for Itga-9, wherein the binding agent specific for Itga-9 is an antibody or antibody fragment or is an anti-Itga-9 RNAi molecule, and
wherein the administration results in reduction in Itga-9 expression and reduction in lymphatic valve formation in the transplant tissue as compared to a transplanted tissue that was not treated with the anti-Itga-9 therapeutic agent.

2. The method of claim 1, further comprising administering an anti-VEGFR-3 agent, wherein the agent specifically binds VEGFR-3.

3. The method of claim 2, wherein the anti-VEGFR-3 agent comprises an anti-VEGFR-3 antibody.

4. The method of claim 1, wherein the administration is by subconjunctival, intraocular, periocular, intraperitoneal, retrobulbar, intramuscular, topical, intravenous, or subcutaneous administration.

5. The method of claim 1, wherein the administration is by local or systemic administration.

6. The method of claim 2, wherein the mammal is a human.

7. The method of claim 3, wherein the anti-VEGFR-3 agent antibody binds to human VEGFR-3.

8. The method of claim 1, wherein the tissue for transplant comprises skin.

9. The method of claim 1, wherein the tissue for transplant comprises a cornea.

10. The method of claim 7, wherein the blocking antibody and the anti-VEGFR-3 agent are sufficient to provide a synergistic response to reduce vessel formation and graft rejection following transplantation.

11. The method of claim 7, wherein the mammal has a high-risk transplant.

12. The method of claim 7, wherein the anti-VEGFR-3 agent and the blocking antibody to human Itga-9 is a bispecific antibody.

13. The method of claim 1, wherein the anti-Itga-9 therapeutic agent comprises a binding agent specific for Itga-9.

14. The method of claim 1, wherein the mammal is a human.

* * * * *